(12) United States Patent
Tanaka

(10) Patent No.: US 7,231,073 B2
(45) Date of Patent: Jun. 12, 2007

(54) MEDICAL IMAGE PROCESSING APPARATUS WITH A FUNCTION OF MEASUREMENT ON A MEDICAL IMAGE

(75) Inventor: Toyoaki Tanaka, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 832 days.

(21) Appl. No.: 10/405,490

(22) Filed: Apr. 3, 2003

(65) Prior Publication Data

US 2003/0215122 A1  Nov. 20, 2003

(30) Foreign Application Priority Data

Apr. 3, 2002  (JP) ............................. 2002-100758

(51) Int. Cl.
*G06K 9/00*  (2006.01)

(52) U.S. Cl. ..................... 382/128; 382/168; 378/140

(58) Field of Classification Search ............... 382/128, 382/129, 130, 131, 132, 133, 134, 154, 168, 382/199, 201, 203, 209, 232, 260, 274, 282, 382/305; 606/86, 63; 604/500; 623/17, 623/16; 378/98.9, 140

See application file for complete search history.

(56) References Cited

U.S. PATENT DOCUMENTS 6,608,917 B1 * 8/2003 Wei et al. ................... 382/132
6,783,530 B1 * 8/2004 Levy ........................... 606/63
6,899,716 B2 * 5/2005 Cragg ......................... 606/86
7,014,633 B2 * 3/2006 Cragg ......................... 604/500
7,046,830 B2 * 5/2006 Gerard et al. ............... 382/128
7,094,258 B2 * 8/2006 Lambrecht et al. ....... 623/17.16
7,095,881 B2 * 8/2006 Lelong et al. ............... 382/132

FOREIGN PATENT DOCUMENTS

| JP | 63-242235 | 10/1988 |
|---|---|---|
| JP | 64-27546 | 1/1989 |

* cited by examiner

*Primary Examiner*—Seyed Azarian
(74) *Attorney, Agent, or Firm*—Oblon, Spivak, McClelland, Maier & Neustadt, P.C.

(57) ABSTRACT

A medical image processing apparatus processes a medical image resulting from a medical image equipment. The apparatus comprises an interface, a processor, and a calculator. The interface is configured to obtain the medical image. The processor is configured to determine a smooth line along an embowed part of a specimen in the medical image obtained by the interface. The calculator is configured to calculate a bow scale of the embowed part based on the smooth line determined by the processor.

59 Claims, 16 Drawing Sheets

(A) (B)

(A)

(B)

(C)

(A)

(B)

MEDICAL IMAGE PROCESSING APPARATUS WITH A FUNCTION OF MEASUREMENT ON A MEDICAL IMAGE

CROSS-REFERENCE TO RELATED APPLICATION

This application is based upon and claims the benefit of priority from prior Japanese Patent Application No. P2002-100758, filed on Apr. 3, 2002, the entire contents of which are incorporated herein by reference.

FIELD OF THE INVENTION

The present invention relates to a medical image processing apparatus which is operative to measure a predetermined part on a medical image obtained through a medical image equipment, such as, for example, an X-ray diagnosis apparatus. The present invention further relates to a method of measuring the predetermined part on the medical image obtained through the medical image equipment.

BACKGROUND OF THE INVENTION

Medical image diagnoses have been rapidly progressing as computers have been improved since 1970's. The medical image diagnoses are accomplished by, for example, an X-ray diagnosis apparatus, an magnetic resonance imaging (MRI) apparatus, an X-ray computed tomography (CT) apparatus, or the like. Nowadays such diagnoses play a very important role for the medical practice. Medical images obtained by medical image equipments, such as those mentioned above, are usually observed and interpreted by a doctor or the like in his or her medical image diagnosis. In addition, the medical images may also be used, as a part of the diagnosis, for measuring a predetermined part of a patient's body, such as a organ and a bone. In a diagnosis of scoliosis as an example of bones diagnoses, a bow scale of the spine is calculated based on transmission images obtained in an X-ray diagnosis apparatus. It is said that scoliosis may occur when a spinal cord grows faster than its peripheral organs. Scoliosis tends to appear particularly in adolescent children who, therefore, are required a once-a-month follow-up.

FIG. 1 is an illustration showing examples of measuring techniques of a bow scale in a diagnosis of scoliosis according to a prior art of the present invention. FIG. 1(A) shows a measurement of the Cobb angles on a radiograph (image) of a patient or an examination object (hereinafter referred to as a specimen) for calculating bow angles. FIG. 1(B) shows a measurement of the 'Vertical-alignment' distances on a radiograph (image) of the specimen for calculating deviations from a representative straight line along a spine, which is one as a hypothetically ideal healthy straight spine along a body axis of the specimen (hereinafter referred to as a median line). The median line may therefore be determined to indicate a center of a body axis of the specimen. The bow scale such as, for example, the Cobb angle and the 'Vertical-alignment' distance shows how much the spine is bent or curved. Basics of the Cobb angle and the 'Vertical-alignment' distance have been established and methods of such measurements are standards known in the art.

In the Cobb angle calculation, as shown in FIG. 1(A), an operator, such as a doctor or a radiological technologist, observes an X-ray transmission image (hereinafter referred to as an image) displayed in a display. The operator then determines by the eye (or determines with his or her sense) one or more points, such as points 1 to 3, which are least bent points of a spine 4 (as long as the operator believes). Each adjacent two least bent points have a most bent point of the spine 4 between the each adjacent two points, based on the displayed image. At the determined points 1 to 3, the operator manually draws perpendicular lines 5 to 7 perpendicular to tangent lines 8 to 10, respectively, using, for example, a mouse. In detail, the operator determines the point 1, and draws the tangent line 8 at the point 1. Further, the operator draws the perpendicular line 5 perpendicular to the tangent line 8. Similarly, the operator draws the perpendicular line 6 perpendicular to the tangent line 9 drawn at the determined point 2. Still further, the operator draws the perpendicular line 7 perpendicular to the tangent line 10 drawn at the determined point 3. A medical image processing apparatus connected to the display calculates angles α and β created by the perpendicular lines 5 to 7. Namely, the perpendicular lines 5 and 6 cross with the angle α and similarly the perpendicular lines 6 and 7 cross with the angle β. The calculated angles α and β are displayed in the display.

In the distance calculation of 'Vertical-alignment', as shown in FIG. 1(B), the operator observes an image displayed in the display and draws a median line 11 along the spine 4. The median line 11 is guessed and determined by the eye of the operator, based on the displayed image. The median line 11 intersects with the spine 4 at intersection points 12 to 14. Then, the operator determines by the eye points 15 and 16 of the spine 4, each of which is the furthest (as long as the operator believes) from the median line 11 between each two adjacent intersection points of the intersection points 12 to 14 when perpendicular lines are dropped to the median line 11 from the points 15 and 16. In more detail, the operator determines the point 15 which is between the intersection points 12 and 13. Further, the operator determines the point 16 which is between the intersection points 13 and 14. The medical image processing apparatus calculates a distance 17 between the point 15 and the median line 11 when the perpendicular line is dropped to the median line 11 from the point 15. Similarly, the medical image processing apparatus calculates a distance 18 between the point 16 and the median line 11 when the perpendicular line is dropped to the median line 11 from the point 16. The calculated distances 17 and 18 are displayed in the display.

In the prior art, scoliosis has been diagnosed using the calculated angles and/or distances as an index of the bow scale. The Cobb angle and the 'Vertical-alignment' distance have been conventionally obtained for the diagnosis of scoliosis based on the points and lines, which were selected and drawn in accordance with the determination by the operator's sense.

Concretely, in the Cobb angle calculation, the points 1 to 3 of the spine 4 in the image displayed in the display were selected based on the operator's sense by observing the image with his or her eyes. Further, the tangent lines 8 to 10 and the perpendicular lines 5 to 7 were drawn based on the operator's sense by observing the image with his or her eyes. Similarly, in the 'Vertical alignment' distance calculation, the median line 11 was drawn based on the operator's sense by observing the image with his or her eyes. Further, the points 15 and 16 were selected based on the operator's sense by observing the image with his or her eyes.

Therefore, the selected points and/or the drawn lines are quite subjective and accordingly the calculated result may be likely to be different among operators. Further, even when it is done by the same operator, the same result may not be reproduced if the operator does not have a clear standard for his or her determination of the selection and/or the drawing. Particularly, as mentioned above, the case of scoliosis may require the once-a-month follow-up of the bow scale of the spine. Therefore, the reproducibility should be kept and is a very important factor for the diagnosis of the scoliosis.

One of factors contributing to the difficulty of the reproducibility (or the deterioration of the calculation accuracy) through the human being system may be as follows. The calculation is made for a very limited tiny region compared to the whole image displayed in the display. In addition, the state of bow of the spine is usually subtle and may be sometimes beyond the discrimination of the human beings. Therefore, the accuracy of the measurement result may not be assured in some cases.

BRIEF SUMMARY OF THE INVENTION

According to a first aspect of the present invention, there is provided a medical image processing apparatus which processes a medical image resulting from a medical image equipment. The apparatus comprises an interface configured to obtain the medical image, a processor configured to determine a smooth line along an embowed part of a specimen in the medical image obtained by the interface, and a calculator configured to calculate a bow scale of the embowed part based on the smooth line determined by the processor.

According to a second aspect of the present invention, there is provided a method of measuring a predetermined part in a medical image resulting from a medical image equipment. The method comprises steps of determining a smooth line along a embowed part of a specimen in the medical image, and automatically calculating a bow scale of the embowed part based on the smooth line.

According to a third aspect of the present invention, there is provided a computer program product on which is stored a computer program for measuring a predetermined part in a medical image resulting from a medical image equipment. The computer program has instructions, which when executed, perform steps comprising determining a smooth line along a embowed part of a specimen in the medical image, and automatically calculating a bow scale of the embowed part based on the smooth line.

According to a fourth aspect of the present invention, there is provided a medical image processing apparatus which processes a medical image resulting from a medical image equipment. The apparatus comprises an interface configured to obtain the medical image, a first processor configured to extract a profile of each vertebra of a spine in the medical image by a pattern recognition processing and obtain a gradient, against a horizontal line, of each of the vertebrae of the spine based on the extracted profile of each of the vertebrae, and a second processor configured to calculate a greatest angle, as a bow scale, between a first of the vertebrae of the spine with a positive gradient sign and a second of the vertebrae of the spine with a negative gradient sign based on the gradient of each of the vertebrae obtained by the first processor.

According to a fifth aspect of the present invention, there is provided a method of measuring a predetermined part in a medical image resulting from a medical image equipment. The method comprises steps of extracting a profile of each vertebra of a spine in the medical image by a pattern recognition processing, obtaining a gradient, against a horizontal line, of each of the vertebrae of the spine based on the extracted profile of each of the vertebrae, and calculating a greatest angle, as a bow scale, between a first of the vertebrae of the spine with a positive gradient sign and a second of the vertebrae of the spine with a negative gradient sign based on the gradient of each of the vertebrae obtained by the first processor.

According to a sixth aspect of the present invention, there is provided an X-ray diagnosis apparatus which comprises a generator, a detector, a mechanism, a synthesizer, a processor, and a calculator. The generator is configured to generate an X-ray. The detector is configured to detect a transmission X-ray transmitted from a specimen resulting from exposure of the X-ray to the specimen. The mechanism is configured to move the generator and the detector so as to obtain a plurality of images of an embowed part of the specimen based on the detected transmission X-ray. The synthesizer is configured to synthesize the plurality of images and output a synthesized image as an embowed part image. The processor is configured to determine a smooth line along the embowed part in the embowed part image. The calculator is configured to calculate a bow scale of the embowed part based on the smooth line.

According to a seventh aspect of the present invention, there is provided a method of measuring a predetermined part in an X-ray image resulting from an X-ray diagnosis apparatus. The method comprises steps of generating an X-ray by a generator, detecting, by a detector, a transmission X-ray transmitted from a specimen resulting from exposure of the X-ray to the specimen, moving the generator and the detector so as to obtain a plurality of images of an embowed part of the specimen based on the detected transmission X-ray, synthesizing the plurality of images, outputting a synthesized image as an embowed part image, determining a smooth line along the embowed part in the embowed part image, and calculating a bow scale of the embowed part based on the smooth line.

BRIEF DESCRIPTION OF THE DRAWINGS

A more complete appreciation of embodiments of the present invention and many of its attendant advantages will be readily obtained by reference to the following detailed description considered in connection with the accompanying drawings, in which.

DETAILED DESCRIPTION OF THE PREFERRED EMBODIMENTS

Embodiments of the present invention will be described with reference to the accompanying drawings. In the embodiments of the present invention, it will be described that an X-ray diagnosis apparatus including a medical image processor may make it possible to accurately measure, as a bow scale, a bow angle of a spine and a deviant distance from a median line due to a bow of the spine. Embodiments of the present invention will be described using an example scoliosis measurement. Embodiments, however, of the present invention may not be limited to scoliosis, but may also be applied to cases, such as, for example, kyphosis, lordosis, bow legs, and any other defectiveness of bones, if it is applicable.

(First Embodiment)

Figure 1:
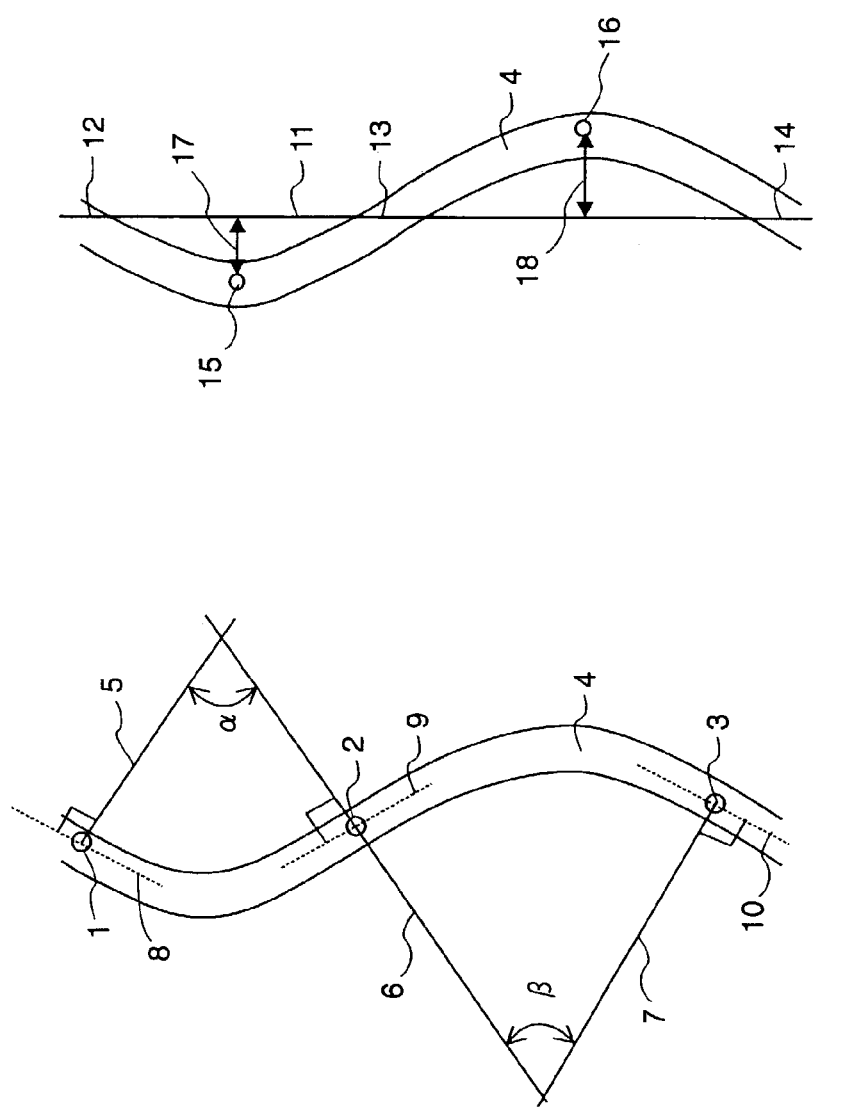
FIG. 1 is an illustration showing examples of measuring techniques of a bow scale in a diagnosis of scoliosis according to a prior art of the present invention.
Figure 2:
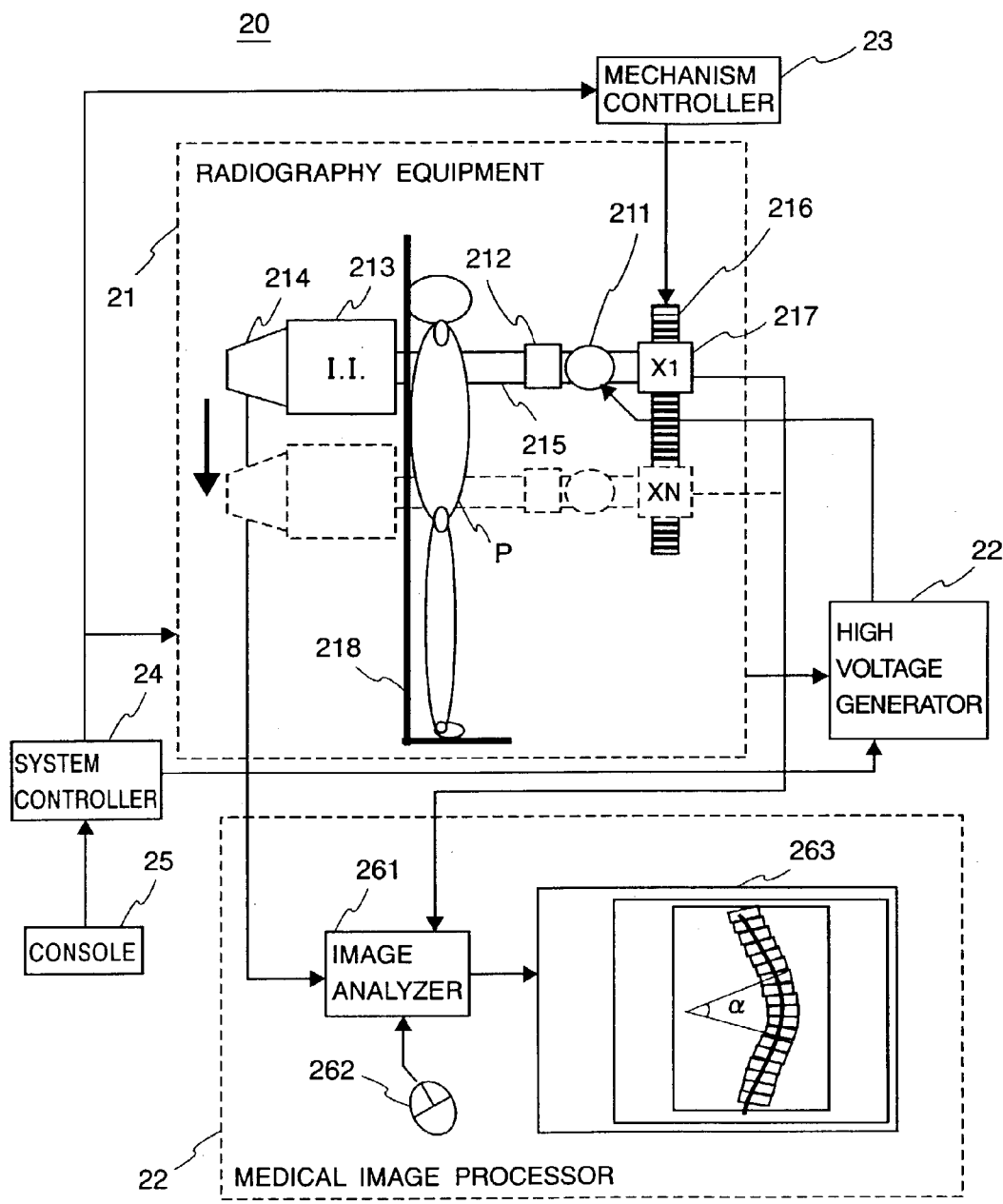
FIG. 2 is a block diagram showing an exemplary configuration of an X-ray diagnosis apparatus including a medical image processor according to a first embodiment of the present invention.

FIG. 2 is a block diagram showing an exemplary configuration of an X-ray diagnosis apparatus including a medical image processor according to a first embodiment of the present invention. An X-ray diagnosis apparatus 20 may include a radiography equipment 21, a high-voltage generator 22, a mechanism controller 23, a system controller 24, a console 25, and a medical image processor 26. The radiography equipment 21 performs an X-ray radiography against a specimen P. The high-voltage generator 22 generates high-voltages which are necessary for the radiography equipment 21 to radiate an X-ray. The mechanism controller 23 controls a mechanism section of the radiography equipment 21 in response to designation signals from the console 25. The system controller 24 performs overall controls for the X-ray diagnosis apparatus 20 including, particularly, the radiography equipment 21, the high-voltage generator 22, and the mechanism controller 23. The console 25 provides various components of the X-ray diagnosis apparatus with designation signals. The medical image processor 26 analyzes and processes images obtained in the radiography equipment 21.

The radiography equipment 21 may be divided into three sections. The three sections may be called an X-ray generating section, an X-ray detecting section, and the mechanism section which moves the X-ray generating section and the X-ray detecting section, respectively.

The X-ray generating section of the radiography equipment 21 may include an X-ray tube 211 and a collimator 212. The X-ray tube 211 radiates (or generates) an X-ray to the specimen P. The collimator 212 collimates the X-ray radiated from the X-ray tube 211. In detail, the X-ray tube 211 comprises a vacuum bulb. In the vacuum bulb, electrons are accelerated with high voltages supplied by the high-voltage generator 22 and are collided with a Tungsten target. Accordingly, the X-ray is generated from the vacuum bulb. The collimator 212 is provided between the X-ray tube 211 and the specimen P. The collimator 212 narrows down the X-ray radiated from the X-ray tube 211 for a predetermined image reception size so as to provide a clear image.

The X-ray detecting section of the radiography equipment 21 may include an X-ray image intensifier (hereinafter referred to as an I.I.) 213 and an X-ray TV camera 214. The X-ray radiated from the X-ray tube 211 is exposed to the specimen P through the collimator 212 and is transmitted from the specimen P as a transmission X-ray. The I.I. 213 receives the transmission X-ray and transforms the transmission X-ray to optical images. The TV camera 214 converts the optical images into electronic signals (or video signals). The electronic signals are output to the medical image processor 26. The X-ray generating section and the X-ray detecting section are connected and supported by a supporter 215. The X-ray generating section, the X-ray detecting section, and the supporter 215 are hereinafter called a radiography system.

The mechanism section may include a movement mechanism 216 and a mechanism position detector 217. The mechanism section is controlled by the mechanism controller 23 which may be provided outside the radiography equipment 21. The movement mechanism 216 moves the radiography system along the body axis of the specimen P. The mechanism position detector 217 detects a position of the radiography system by counting the number of pulses output from an encoder furnished with the movement mechanism 216. In addition, the mechanism position detector 217 outputs detection information to an external unit and also drives the high-voltage generator 22 so as to make the X-ray tube 211 radiate the X-ray.

The radiography equipment 21 further includes a bed 218. The bed 218 is usually a table supporting the specimen P during the radiography. The bed 218 may be made of materials which easily allow the X-ray to transmit the bed 218. Generally, the radiography is implemented for the specimen P in an erect position which gives a force of gravity against the specimen P in a diagnosis of the scoliosis. Therefore, the bed 218 may be used as a footrest for the specimen P, as shown in FIG. 2.

The high-voltage generator 22 generates high-voltages to be supplied to the X-ray tube 211 and to be impressed between an anode and a cathode of the X-ray tube 211 so as to accelerate thermal electrons. The thermal electrons are generated from the cathode of the X-ray tube 211. The high-voltage generator 22 is capable of a large power, for example, 80 KW to 100 KW, by an inverter system. The high-voltage generator 22 may also include an interface for informing the medical image processor 26 about timings of image data acquisition.

The mechanism controller 23 controls the movement mechanism 216 based on designation signals from the console 25 through the system controller 24. The mechanism controller 23 may control a moving speed and/or a moving direction of the radiography system along the body axis of the specimen P.

The system controller 24 performs overall controls for the X-ray diagnosis apparatus 20 including controls of the image data acquisition and the mechanism movement based on the designation signals from the console 25. The system controller 24 further includes controls of transferring acquired image data to the medical image processor 26.

The console 25 includes various switches and buttons, a keyboard, and a display panel. The console 25 may be operated by an operator, such as a doctor or a radiological technologist. Operations by the operator may include designations of radiography conditions and of movement of the mechanism section. The designation signals based on such operations are sent to each unit or component of the X-ray diagnosis apparatus 20 through the system controller 24.

The medical image processor 26 may include an image analyzer 261, a mouse 262, and a display 263. The image analyzer 261 synthesizes (or combines) a plurality of image data acquired in the radiography system and calculates Cobb angles, 'Vertical-alignment' distances, and/or the like based on synthesized image data. The mouse is connected to the image analyzer 261 and is operative, by the operator, to input to the image analyzer 261 information necessary for the image calculation. The display 263 displays a synthesized image and calculation results. The detail of the medical image processor 26 will be described with reference to FIG. 3.

According to the first embodiment and also the following embodiments of the present invention, the medical image processor 26 will be described as a part of the X-ray diagnosis apparatus 20. Embodiments of the present invention, however, may not be limited to such a use of the medical image processor. The medical image processor may be used as an independent medical image processing apparatus according to embodiments of the present invention. For example, the independent medical image processing apparatus may be connected to one or more medical image equipments such as X-ray diagnosis apparatuses through a network. Further, the independent medical image processing apparatus may be provided in a place remote from an X-ray diagnosis apparatus without the medical image processor 26. The remote place can be, for example, a different room, a different floor, a different hospital, a doctor's home, or any other medical facility. Still further, the medical image processor 26 or its processing features may also be installed in a workstation for interpreting medical images or in any other computerized equipment with or without features for specific purposes. In any cases, the medical image processor or the medical image processing apparatus may process images obtained through a network or images obtained from a storage media as off-line data.

Figure 3:
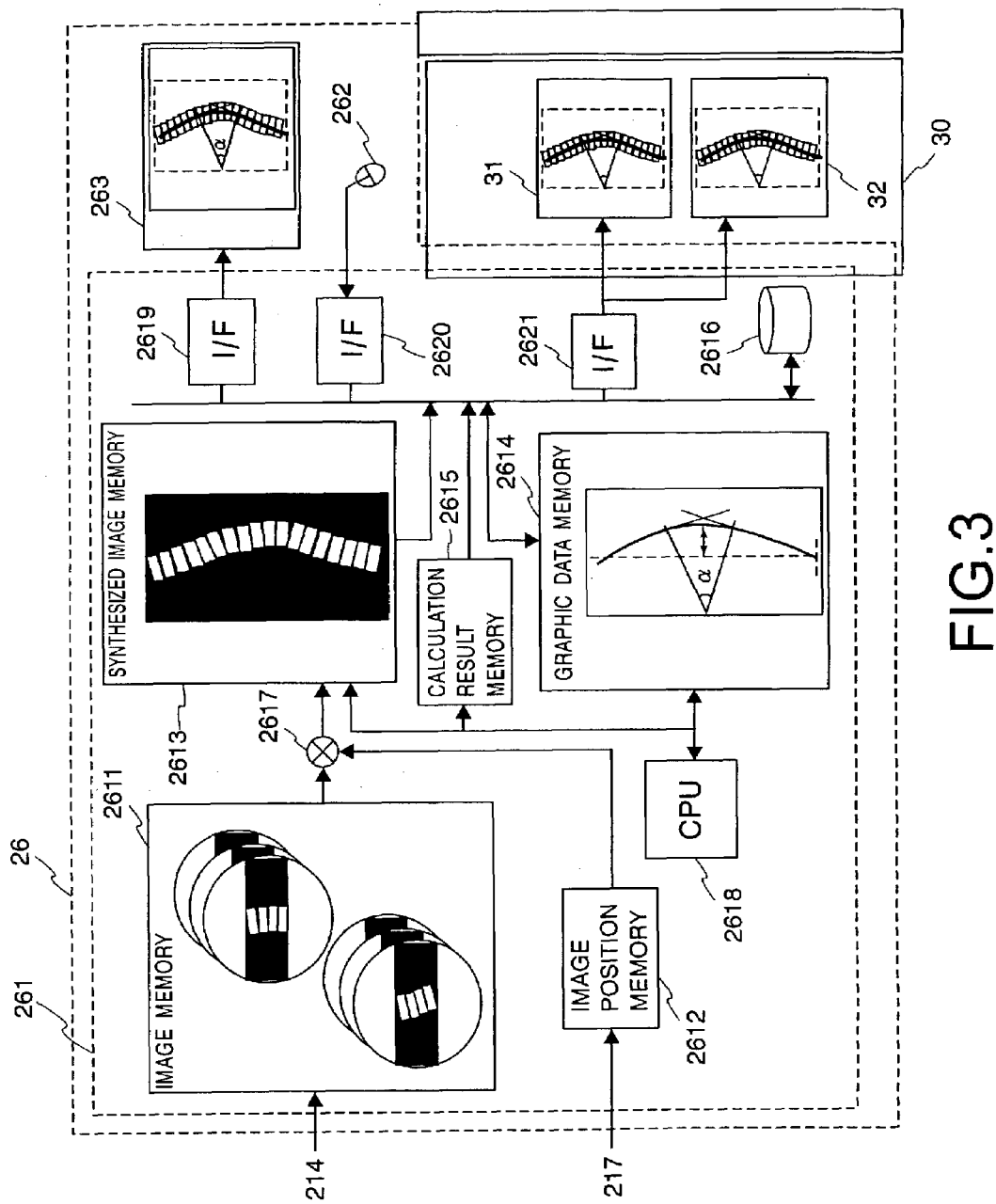
FIG. 3 is a block diagram showing an exemplary configuration of a medical image processor according to the first embodiment of the present invention.

FIG. 3 is a block diagram showing an exemplary configuration of the medical image processor 26 according to the first embodiment of the present invention. FIG. 3 also shows external equipments, such as an image workstation and a laser imager, which can be connected to the medical image processor 26 (the X-ray diagnosis apparatus 20).

The image analyzer 261 may comprise a memory section, a calculation section, and an interface section.

The memory section of the image analyzer 261 may include an image memory 2611, an image position information memory 2612, a synthesized image memory 2613, a graphic data memory 2614, a calculation result memory 2615, and a hard disk 2616. The image memory 2611 stores the plurality of image data of the specimen P. The image position information memory 2612 stores position information of the image data stored in the image memory 2611. In other words, the image position information memory 2612 stores information regarding the position of the specimen when each image data have been acquired. The synthesized image memory 2613 stores the synthesized image data. The graphic data memory 2614 stores graphic data (or overlay data). The calculation result memory 2615 stores a result of calculations of the Cobb angles and the 'Vertical-alignment' distances. The hard disk 2616 stores information or data, such as the synthesized image data, the graphic data, and the result of calculations.

The calculation section of the image analyzer 261 may include an image synthesizer 2617 and a CPU (Central Processing Unit) 2618. The image synthesizer 2617 synthesizes the plurality of image data stored in the image memory 2611 in accordance with the position information stored in the image position information memory 2612 and outputs the synthesized image data to the synthesized image memory 2613. The CPU 2618 calculates the Cobb angles and/or the 'Vertical-alignment' distances based on the synthesized image data, and outputs a result of the calculations to the calculation result memory 2615.

The interface section of the image analyzer 261 may include a display interface 2619, an operation input interface 2620, and a communication interface 2621. The display interface 2619 interfaces for displaying a synthesized image, the graphic data, the result of calculation, and/or the like in the display 263. The display interface 2619 may further add or synthesize the synthesized image data with the graphic data and further with the result of calculation. The operation input interface 2620 interfaces, for example, a connection with the mouse 262. The communication interface 2621 interfaces a connection with an external equipment 30, such as, for example, a workstation 31 and a laser imager 32.

The display 263 displays data and information stored in the synthesized image memory 2613, the graphic data memory 2614, the calculation result memory 2615, and/or the hard disk 2616, through the display interface 2620.

The mouse 262 may be used as an input device, interactively responding to various menu displayed in the display 263. In addition, the mouse 262 may also be used for manually tracing the spine displayed as a part of the synthesized image and for setting a range of pattern recognition according to embodiments of the present invention. The tracing and the pattern recognition will be described later.

In the following description, components of the image analyzer 261 will be further explained in more detail.

The image memory 2611 may be a semiconductor memory for the plurality of image data (transmission image data) radiographed while the radiography system is moving along the body axis of the specimen P. The image data may be stored in the image memory 2611 in a form of electronic (or video) signals converted into digital signals in the X-ray TV camera 214. The image position information memory 2612 stores each position of the radiography system detected by the mechanism position detector 217 when each of the plurality of image data is acquired. In other words, each position information of the plurality of image data is stored in the image position information memory 2612.

The image synthesizer 2617 produces the synthesized image data by synthesizing (or combining) the plurality of image data stored in the image memory 2611 based on the position information of the plurality of image data from the image position information memory 2612. The synthesized image data are output to and stored in the synthesized image memory 2613. Further, the graphic data memory 2614 stores, as graphic data, construction or drawing information (including lines, curves, characters, and the like), which are presented based on drawing instructions by the mouse 262 or calculation results in the CPU 2618. The calculation results are stored in the calculation result memory 2615.

The CPU 2618 is a primary computing unit which sets or determines a spine line based on the construction or the drawing information presented by the operator against the synthesized image displayed in the display 263 and stored in the graphic data memory 2614. Further, the CPU 2618 calculates the Cobb angles and the 'Vertical-alignment' distances based on the construction or the drawing information presented by the operator on the synthesized image displayed in the display 263 and stored in the graphic data memory 2614.

The hard disk 2616 is a device to store the synthesized image data, stored in the synthesized image memory 2613, attending the image position information stored in the image position information memory 2612, the construction or the drawing information (graphic data) stored in the graphic data memory 2614, and the calculation results stored in the calculation result memory 2615.

The display interface 2619 reads out data from the synthesized image memory 2613, the graphic data memory 2614, the calculation result memory 2615, and/or the hard disk 2616. Further, the display interface 2619 converts the read-out data into data in a TV format so as to display the data in the display 263. When the data are displayed in the display 263, only the synthesized image may be displayed in the display 263 through the display interface 2619 in a predetermined first stage. In a predetermined second stage, the display interface 2619 synthesizes the synthesized image with the graphic data. In other words, the display interface 2619 prepares the synthesized image overlaid with the graphic data. The synthesized image overlaid with the graphic data are displayed in the display 263. Similarly, in a predetermined third stage, the display interface 2619 further overlays the calculation results on the synthesized image already overlaid with the graphic data. Such synthesized image overlaid with the calculation results is displayed in the display 263.

The operation input interface 2620 interfaces the information from input devices (such as the mouse 262) for providing the medical image processor 26 with the information. The communication interface 2621 reads out data from the synthesized image memory 2613, the graphic data memory 2614, the calculation result memory 2615, and/or the hard disk 2616. Further, the communication interface 2621 interfaces a transfer of the read-out data to the external equipment 30, such as the workstation 31 and the laser imager 32. The workstation 31 may be a computerized-equipment usually used to interpret images for the purpose of image diagnosis. The laser imager 32 may be used to present images on a film.

Next, processes of operations in the X-ray diagnosis apparatus will be explained with reference to FIGS. 2 to 5, taking a synthesized image of the spine as an example of the first embodiment of the present invention. The human spine is usually known to comprise cervical vertebrae, thoracic vertebrae, lumbar vertebrae, sacral vertebrae, and coccygeal vertebrae. The cervical vertebrae comprise seven vertebrae. The thoracic vertebrae comprise twelve vertebrae. The lumbar vertebrae comprise five vertebrae. The sacral vertebrae comprise five vertebrae. The coccygeal vertebrae comprise three to five vertebrae, which configure a coccygeal bone. Each vertebra is connected to its adjacent vertebra through an intervertebral disk. Therefore, as it is well known, the spine can be curved. When, however, the spine is malfunctioned due to a disease or its growth under an abnormal circumstance, the spine may sometimes be shaped irregularly. Such irregularity may have to be properly diagnosed and be cured.

Figure 4:
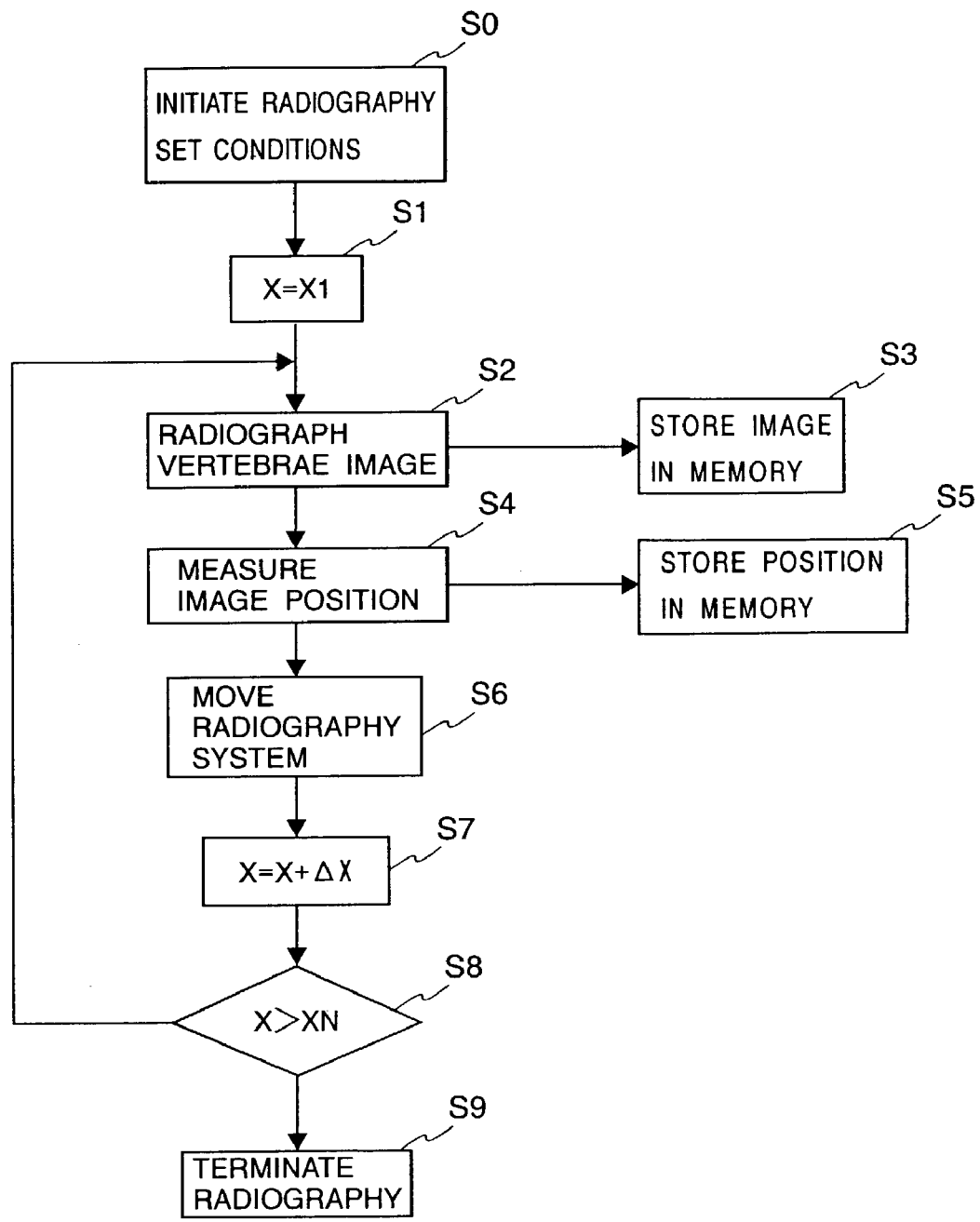
FIG. 4 is a flowchart showing an example of procedures of obtaining images on a spine of a specimen according to the first embodiment of the present invention.
Figure 5:
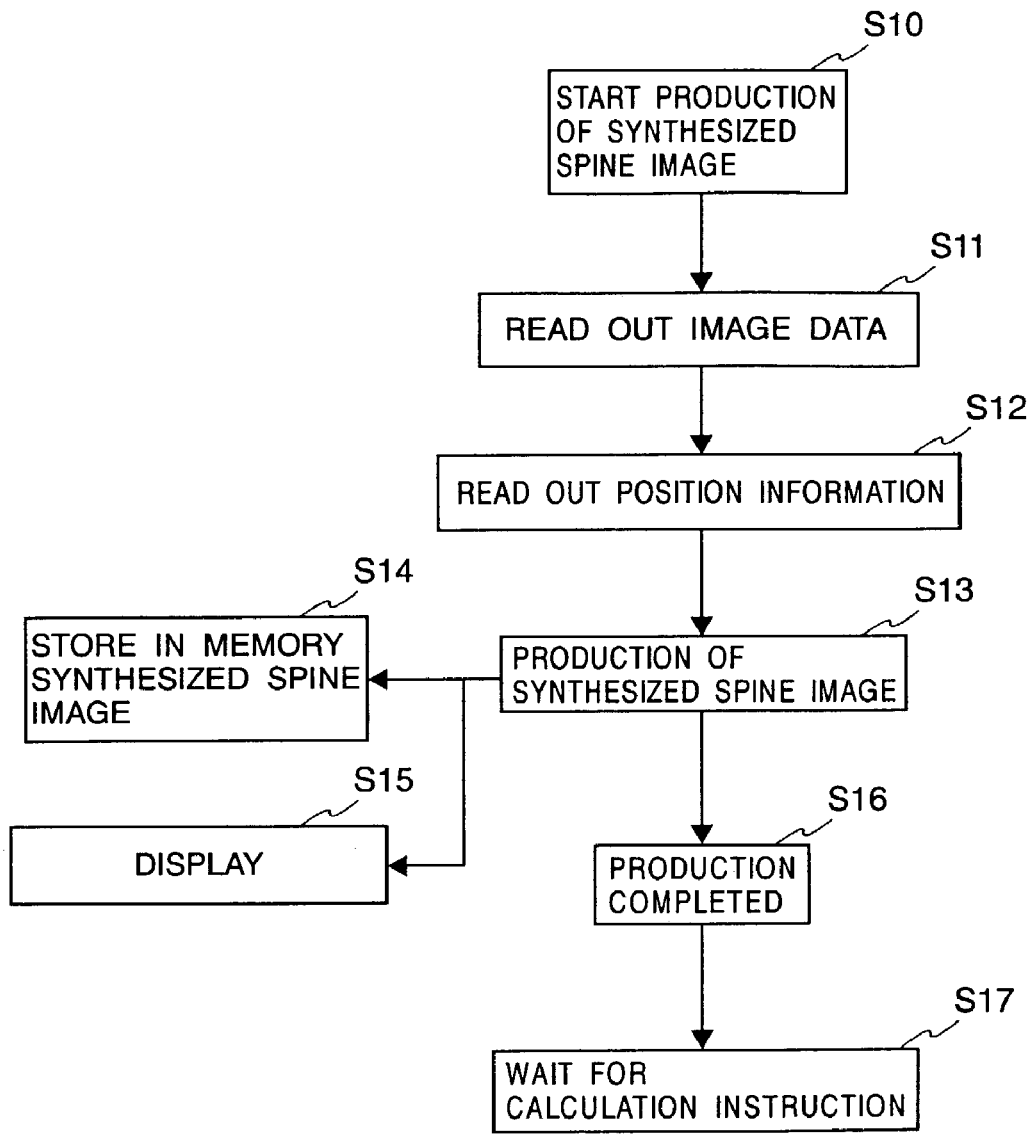
FIG. 5 is a flowchart showing an example of procedures of synthesizing vertebrae images so as to produce a synthesized spine image according to the first embodiment of the present.

FIG. 4 is a flowchart showing an example of procedures of obtaining images on the spine of the specimen P according to the first embodiment of the present invention. FIG. 5 is a flowchart showing an example of procedures of synthesizing vertebrae images so as to produce a synthesized spine image according to the first embodiment of the present invention.

In the following procedures, the radiography may be performed over a range between a first cervical vertebra and a head of femur by moving the radiography system. Accordingly, images of vertebrae can be acquired through the spine.

1. Radiography and Storage of a Plurality of Image Data

Prior to the radiography, radiographic conditions are set with the console 25 by the operator. For example, when the radiography is going to be made at positions X1, X2, . . . , and XN with intervals of Δ X, these N points are set by the console 25. The information of these N points may be sent to the mechanism position detector 217 through the system controller 24 and the mechanism controller 23. The information may be then stored in a memory provided in the mechanism position detector 217 (step S0). Responsive to the information, the mechanism controller 23 controls the radiography system to move to an initial position X1 where the radiography is initiated (step S1). The initial position X1 may be adjacent to the first cervical vertebra.

When a radiograph initiation instruction is given by the console 25 and is provided to the system controller 24, the mechanism position detector 217 generates initial pulses at the initial position X1. The high-voltage generator 22 is driven responsive to the initial pulses. Further, an output of the high-voltage generator 22 drives the X-ray tube 211, and accordingly X-ray pulses are radiated from the X-ray tube 211 and is exposed to the specimen P. This initial exposure may be at the initial position nearby the first cervical vertebra. A transmission X-ray transmitted from the specimen P is received and formed as an initial vertebrae image by the I.I. 213 and is further converted into digitized electronic signals by the X-ray TV camera 214 (step S2). The digitized electronic signals from the X-ray TV camera 214 are sent to the image analyzer 261 of the medical image processor 26 and stored in the image memory 2611 as initial vertebrae image data (step S3). In addition, an instruction for writing in the initial vertebrae image data is sent to the image memory 2611 from the X-ray TV camera 214 in parallel with sending the initial vertebrae image data.

At more or less the same time as the initial vertebrae image data are stored in the image memory 2611, the mechanism position detector 217 outputs signals representing the initial position X1 of the radiography system. The signals are sent to the image analyzer 261 and stored in the image position information memory 2612 of the image analyzer 261 (steps S4 and S5).

When the radiography is finished at the initial position X1, the mechanism controller 23 provides a servomotor of the movement mechanism 216 with driving signals. Accordingly, the radiography system starts to move at a constant speed along the body axis of the specimen P (step S6). Pulses output from the encoder in the radiography system are sent to the mechanism position detector 217. A counter of the mechanism position detector 217 counts the number of the pulses output from the encoder. When the radiography system has moved a distance Δ X, an output of the counter corresponds to data representing a second position X2. Then, the mechanism position detector 217 sends pulses to the high-voltage generator 22 (step S7). In a similar manner to the case of the initial position X1, the radiography system radiographs at the second position X2. Accordingly, second vertebrae image data are acquired and stored in the image memory 2611. Also the mechanism position detector 217 outputs signals representing the second position X2 of the radiography system. The signals are stored in the image position information memory 2612.

After the radiography at the second position X2, the radiography is repeated until a final position XN of the radiography system in a manner similar to the above description (step S8). As a result, the radiography system moves from the position of the first cervical vertebra (the initial position X1) to the position of the head of femur (the final position XN) at the constant speed along the body axis of the specimen P. In accordance with the movement of the radiography system, every time when an integrated value indicated by output pulses of the encoder in the radiography system corresponds to every data representing positions X1, X2, . . . , and XN, the radiography is implemented by the radiography system. The acquired image data (the initial vertebrae image data to a final vertebrae image data) are stored in the image memory 2611. The position information (signals representing the initial position X1 to the final position XN) is stored in the image position information memory 2612. The acquired image data and/or the position information may also be stored in the hard disk 2616. When the image data have been acquired at the positions X1 to XN, the radiography is terminated (step S9).

2. Production and Storage of a Synthesized Spine Image

When the radiography has been completed at the N positions and is terminated, the operator may use the mouse 262 and select a command icon displayed in the display 263, which instructs to produce a synthesized spine image (step S10). Responsive to the command selection, the vertebrae image data (the initial vertebrae image data to the final vertebrae image data) are read out from the image memory 2611 to the image synthesizer 2617 (step S11). Then (alternatively before the step S11) the position information of the initial position X1 to the final position XN is read out from the image position information memory 2612 to the image synthesizer 2617 (step S12).

In the image synthesizer 2617, the vertebrae image data are combined one to the next in accordance with the position information under controls of the CPU 2618. For example, the initial vertebrae image data acquired at the initial position X1 can be followed by the second vertebrae image data acquired at the second position X2. The second vertebrae image data acquired at the second position X2 can be followed by the third vertebrae image data acquired at the third position X3. In a similar manner, all the vertebrae image data is sequentially combined through until the final vertebrae image data XN (step S13). Image data resulting from the combination of the initial to the final vertebrae image data are stored as synthesized spine image data in the synthesized image memory 2613. In detail, each vertebrae image data are sequentially written in the synthesized image memory 2613 in accordance with each write initiation address obtained by reducing each of the position information (i.e. each moved distance of the radiography system) into the number of pixels of the synthesized image memory 2613 (step S14). The synthesized spine image data may be formatted in the display interface 2619 and displayed as a synthesized spine image in the display 263 (step S15).

After the completion of producing the synthesized spine image data (step S16), the medical image processor 26 awaits calculation instructions of either the Cobb angles or the 'Vertical-alignment' distances (step S17). If a calculation of the Cobb angles is instructed responsive to an operator's selection of a Cobb angle calculation command icon displayed in the display 263, the procedures will follow a flowchart shown in FIG. 6. Alternatively, if a calculation of the 'Vertical-alignment' distance is instructed responsive to an operator's selection of a 'Vertical alignment' distance calculation command icon displayed in the display 263, the procedures will follow a flowchart shown in FIG. 10.

3. Calculation of the Cobb Angle

Figure 6:
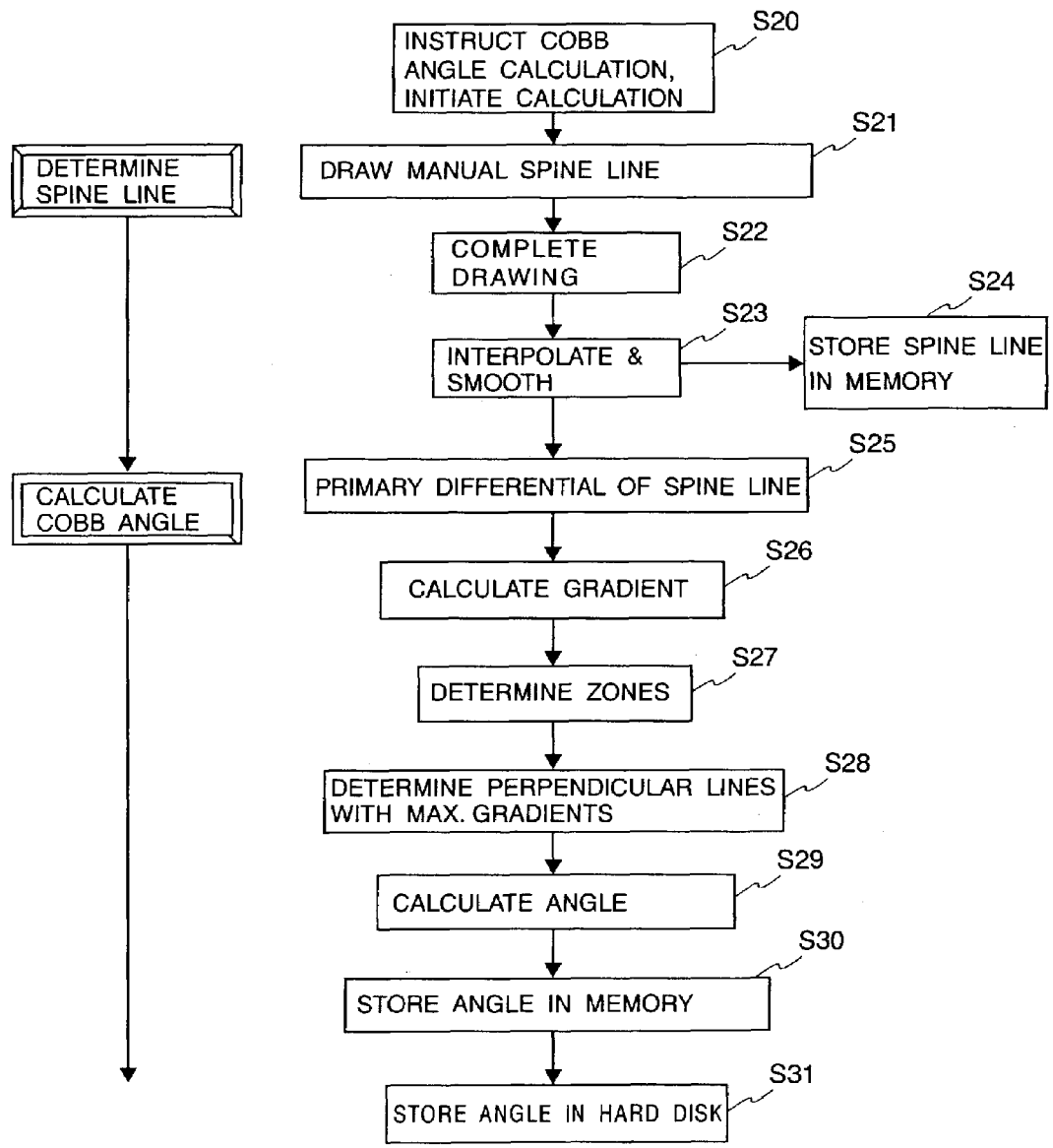
FIG. 6 is a flowchart showing an example of procedures of a Cobb angle calculation according to the first embodiment of the present invention.

Procedures of a Cobb angle calculation will be described with reference to FIG. 6. FIG. 6 is a flowchart showing an example of procedures of the Cobb angle calculation according to the first embodiment of the present invention.

When the operator selects the Cobb angle calculation command icon displayed in the display 263 by using the mouse 262, the Cobb angle calculation is instructed responsive to the operator's selection. The medical image processor 26 prepares to start procedures of the Cobb angle calculation (step S20).

First of all, a spine line is drawn along the spine displayed in the synthesized spine image by the operator. The operator may manually try to draw the spine line along a center of the spine based on his or her sense. The spine line mentioned above is hereinafter referred to as a manual spine line. To draw the manual spine line, the operator may use the mouse 262 and place a cursor of the mouse 262 around a center position of the first cervical vertebra in the synthesized spine image displayed in the display 263. After the operator has determined the cursor position, the operator may click at the cursor position and drag the cursor until a position around the head of femur, trying to keep a center of the spine (step S21). This manual spine line (the track of the drawing) is stored in the graphic data memory 2614 and also in the calculation result memory 2615. In addition, the manual spine line is overlaid on the synthesized spine image data in the display interface 2619. Accordingly, the manual spine line is displayed with the synthesized spine image in the display 263 in real time.

When the operator has completed drawing the manual spine line against the spine in the synthesized spine image displayed in the display 263, he or she may instruct the completeness of the drawing by the mouse 262. Accordingly, signals indicating the completeness are supplied to the CPU 2618 through the mouse 262 (step S22). Responsive to the signals from the mouse 262, the CPU 2618 interpolates and also smoothes the manual spine line. The interpolation and smoothing processing may be accomplished by conventional techniques. Accordingly, a smooth spine line may be obtained (step S23).

Figure 7:
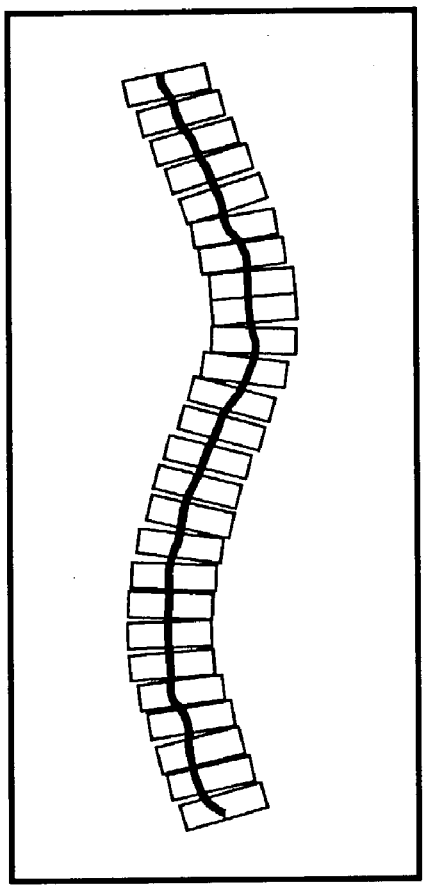
FIG. 7 is an illustration showing an example of a manual spine line and an example of a smooth spine line drawn in the synthesized spine image displayed in a display according to the first embodiment of the present invention.
Figure 7:
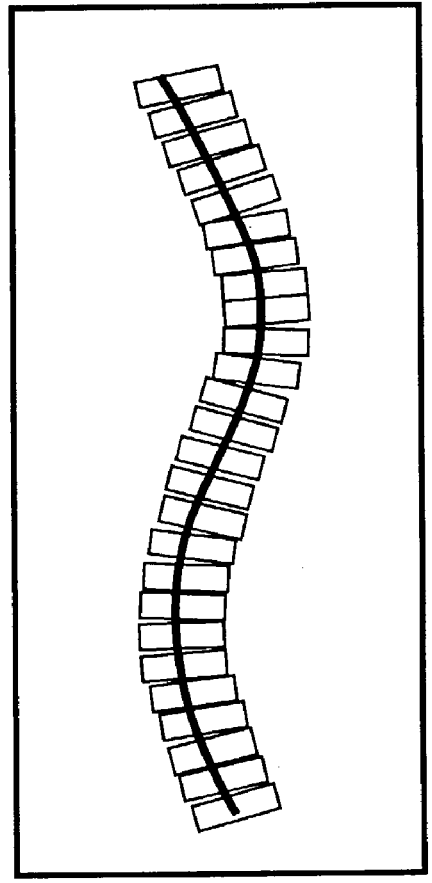

FIG. 7 is an illustration showing an example of the manual spine line and an example of the smooth spine line drawn in the synthesized spine image displayed in the display 262 according to the first embodiment of the present invention. FIG. 7(A) shows the example of the manual spine line drawn by the operator. FIG. 7(B) shows the example of the smooth spine line, which has already been interpolated and smoothed in the CPU 2618. It may be possible to balance out errors caused by the manual operation in the smoothing processing. The smooth spine line data are stored in the graphic data memory 2614 and the calculation result memory 2615 (step S24). In addition, the smooth spine line is displayed in the display 263. In the display 263, the manual spine line may be replaced with the smooth spine line in response to the processing by the CPU 2618. Alternatively, both the manual spine line and the smooth spine line may be displayed side by side.

When the interpolation and smoothing processing has been completed, the CPU 2618 automatically calculates the Cobb angles based on the smooth spine line data stored in the graphic data memory 2614 and the calculation result memory 2615. In the Cobb angle calculation, the CPU 2618 calculates gradients (or angles), against a horizontal line, of perpendicular lines perpendicular to tangent lines at predetermined points on the smooth spine line. As a result, the CPU 2618 obtains perpendicular lines, which have the greatest gradients (angles).

Figure 8:
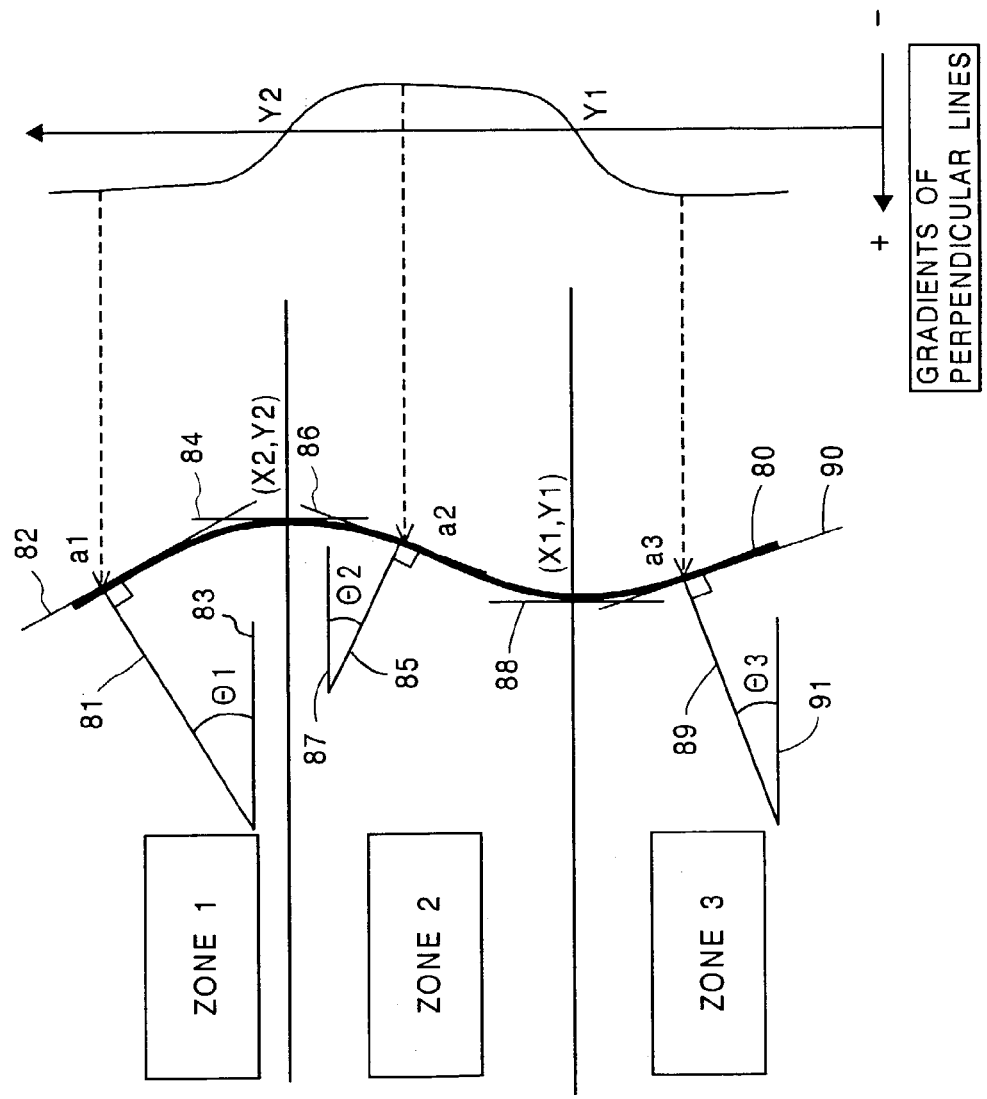
FIG. 8 is an illustration showing an example of the Cobb angle calculation according to the first embodiment of the present invention.

The Cobb angle calculation will be described in more detail with reference to FIG. 8. FIG. 8 is an illustration showing an example of the Cobb angle calculation according to the first embodiment of the present invention. The CPU 2618 calculates primary differentials at predetermined points on the smooth spine line and obtains tangent lines at the predetermined points (step S25). The predetermined points may be determined at predetermined intervals on the smooth spine line, depending on, for example, the resolution of the display 263 or the information included in the smooth spine line data. Next, the CPU 2618 obtains perpendicular lines perpendicular to the tangent lines, respectively. When the perpendicular lines are obtained, the CPU 2618 calculates gradients of the perpendicular lines. In other words, the CPU 2618 calculates angles between a horizontal line and the perpendicular lines. The gradients (and/or angles) may be stored in the calculation result memory 2615 (step S26).

When the gradients of all the perpendicular lines have been obtained, the CPU 2618 divides the smooth spine line into two or more zones in accordance with signs of the gradients. As shown in FIG. 8, a sign of the gradients above a y-coordinate Y2 along the Y-axis is positive. Therefore, this part of a smooth spine line 80 may be categorized as a zone 1. At coordinates (X2, Y2) and (X1, Y1), the gradients become zero (0). Further, a sign of the gradients between y-coordinates Y2 and Y1 is negative. Therefore, this part of the smooth spine line 80 may be categorized as a zone 2. Similarly, since a sign of the gradients is positive again below a y-coordinate Y1, this part of the smooth spine line 80 may be categorized as a zone 3 (step S27).

After the determination of the zones, the CPU 2618 selects one of the perpendicular lines perpendicular to the tangent lines at the predetermined points on the part of the smooth spine line 80, which belongs to the zone 1. The one perpendicular line to be selected can be a perpendicular line with a greatest gradient in the zone 1. In FIG. 8, for example, a perpendicular line 81 is selected. The perpendicular line 81 is perpendicular to a tangent line 82 at a tangent point a1 on the smooth spine line 80. The perpendicular line 81 produces an angle θ 1 against a horizontal line 83. At a tangent point (X2, Y2), a gradient of a perpendicular line (not shown) perpendicular to a tangent line 84 becomes zero as mentioned above. Regarding the zone 2, the CPU 2618 also selects one of the perpendicular lines perpendicular to the tangent lines at the predetermined points on the part of the smooth spine line 80, which belongs to the zone 2. The one perpendicular line to be selected can be a perpendicular line with a greatest gradient in the zone 2. Again in FIG. 8, for example, a perpendicular line 85 is selected. The perpendicular line 85 is perpendicular to a tangent line 86 at a tangent point a2 on the smooth spine line 80. The perpendicular line 85 produces an angle θ 2 against a horizontal line 87. At a tangent point (X1, Y1), a gradient of a perpendicular line (not shown) perpendicular to a tangent line 88 becomes zero as mentioned above. Still further, in the zone 3, the CPU 2618 still selects one of the perpendicular lines perpendicular to the tangent lines at the predetermined points on the part of the smooth spine line 80, which belongs to the zone 3. The one perpendicular line to be selected can be a perpendicular line with a greatest gradient in the zone 3. Again in FIG. 8, for example, a perpendicular line 89 is selected. The perpendicular line 89 is perpendicular to a tangent line 90 at a tangent point a3 on the smooth spine line 80. The perpendicular line 89 produces an angle θ 3 against a horizontal line 91 (step S28).

Figure 9:
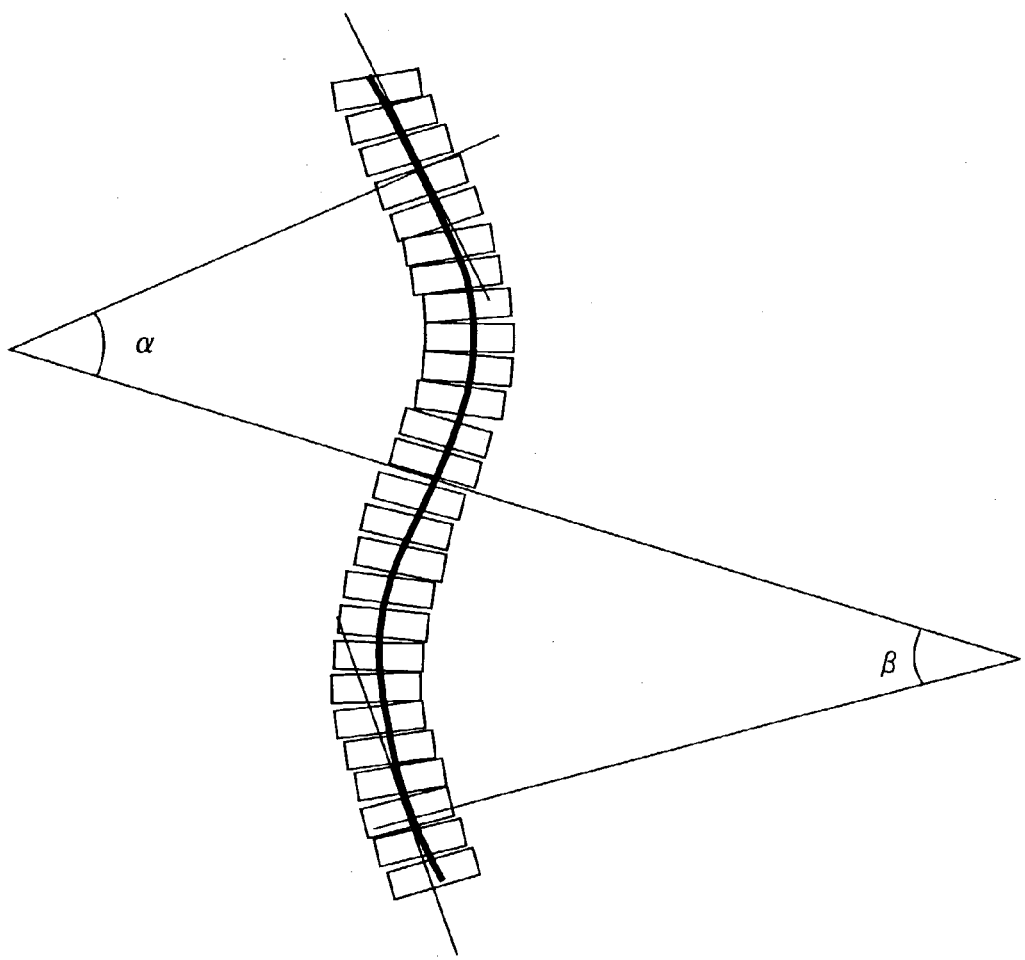
FIG. 9 is an illustration showing an example of graphic data regarding the Cobb angle according to the first embodiment of the present invention.

With those angles θ 1 to θ 3, the CPU 2618 calculates the Cobb angles. A first Cobb angle α is obtained by adding an absolute angle of the angle θ 1 and an absolute angle of the angle θ 2. Similarly, a second Cobb angle β is obtained by adding an absolute angle of the angle θ 2 and an absolute angle of the angle θ 3 (step S29). These Cobb angle data may be stored in the calculation result memory 2615. Also graphic data including the angles α and β as shown in FIG. 9 may be stored in the graphic data memory 2614 (step S30). In addition to the storage, the graphic data stored in step S30 may be overlaid on smooth spine image data in the display interface 2619. Accordingly, the smooth spine image with the Cobb angle information can be displayed in the display 263. Information regarding the Cobb angle calculation including the Cobb angles and the gradients of the perpendicular lines may be stored as calculation result data in the hard disk 2616 as well as the calculation result memory 2615 (step S31).

4. Calculation of the 'Vertical-Alignment' Distance

Figure 10:
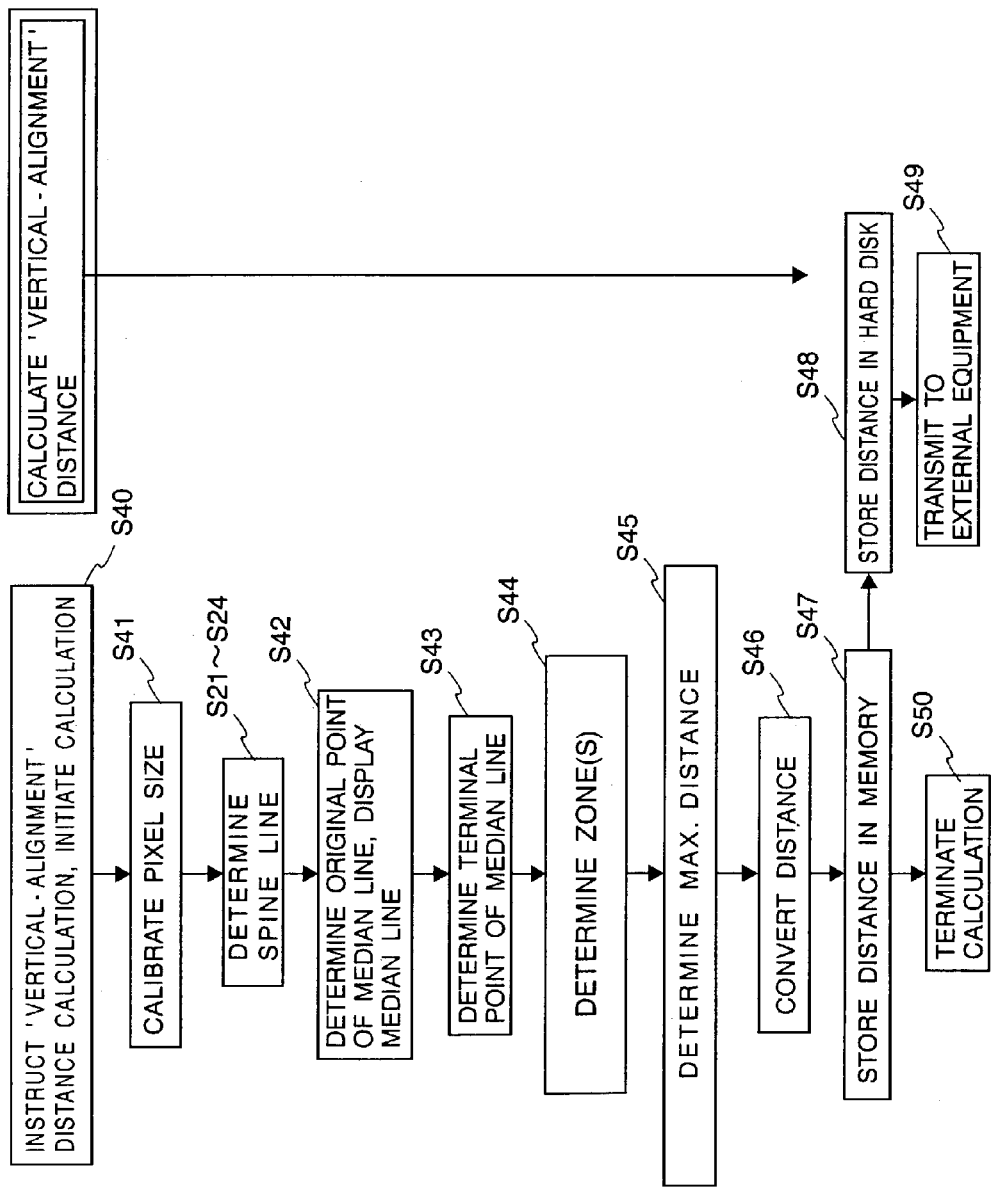
FIG. 10 is a flowchart showing an example of procedures of a 'Vertical-alignment' distance calculation according to the first embodiment of the present invention.

Procedures of a 'Vertical-alignment' distance calculation will be described with reference to FIG. 10. FIG. 10 is a flowchart showing an example of procedures of the 'Vertical-alignment' distance calculation according to the first embodiment of the present invention.

As described in step S17 of FIG. 5, while the medical image processor 26 awaits the calculation instructions, if the operator selects the 'Vertical-alignment' distance calculation command icon displayed in the display 263 by using the mouse 262, the 'Vertical-alignment' distance calculation is instructed responsive to the operator's selection. The medical image processor 26 prepares to start procedures of the 'Vertical-alignment' distance calculation (step S40).

First of all, the CPU 2618 calibrates a relationship between a pixel of the synthesized spine image displayed in the display 263 and an actual distance of the spine of the specimen P. For example, radiography conditions may usually be set in advance of the radiography in accordance with operations in the console 25 by the operator. An expansion ratio of the image determined based on a physical inter-relationship among the X-ray tube 211, the specimen P, and the I.I. 213 may also be set with other conditions at the time when the radiography conditions are set. The expansion ratio of the image can be understood as the number of pixels per a unit length of the image. Therefore, the number of pixels per a unit length of the synthesized spine image displayed in the display 263 may be obtained by performing corrections of expansion or reduction ratio for the synthesized spine image data stored in the synthesized image memory 2613. Accordingly, a conversion ratio may be determined between a length in the display 263 and an actual length (step S41).

After the calibration in step S41, a spine line of the spine in the synthesized spine image is determined in a similar manner to the case of the Cobb angle calculation. The synthesized spine image stored in the synthesized image memory 2613 is displayed in the display 263 through the display interface 2619. The operator may use the mouse 262 and place a cursor of the mouse 262 around a center position of the first cervical vertebra in the synthesized spine image displayed in the display 263. After the operator has determined the cursor position, the operator may click at the cursor position and drag the cursor until a position around the head of femur, trying to keep a center of the spine (step S21 in FIG. 6). When the operator has completed drawing a manual spine line against the spine in the synthesized spine image displayed in the display 263 (step S22 in FIG. 6), the CPU 2618 interpolates and also smoothes the manual spine line. Accordingly, a smooth spine line may be obtained (step S23 in FIG. 6). Smooth spine line data are stored in the graphic data memory 2614 and the calculation result memory 2615 (step S24 in FIG. 6).

Figure 11:
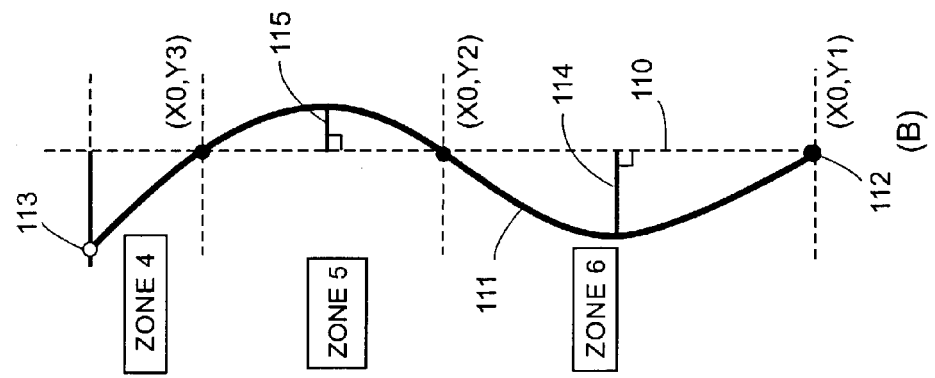
FIG. 11 is an illustration showing an example of the 'Vertical-alignment' distance calculation according to the first embodiment of the present invention.
Figure 11:
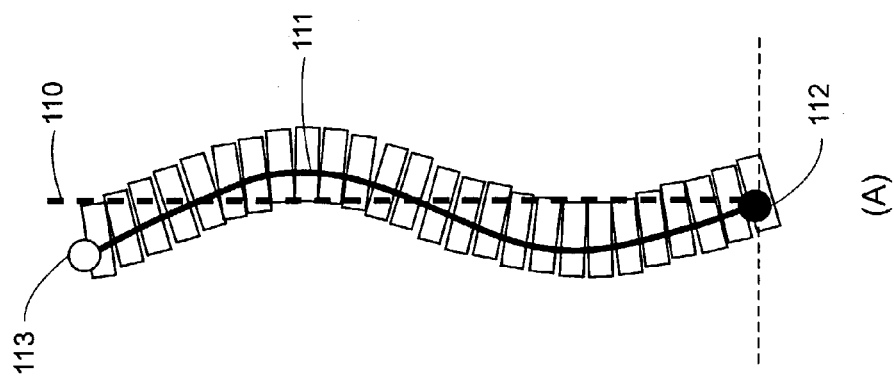

FIG. 11 is an illustration showing an example of the 'Vertical-alignment' distance calculation according to the first embodiment of the present invention. When the smooth spine line data are obtained and overlaid on the synthesized spine image data, a smooth spine image may be displayed in the display 263. With reference to the smooth spine image, the operator may try to draw a median line 110 against a smooth spine line 111 in the smooth spine image. The operator designates an original point 112 of the median line 110 by operating the mouse 262, observing the smooth spine image displayed in the display 263. Although it would be possible to set an original point at the coccygeal bone, which is situated at the bottom of the spine, it is likely to be difficult to recognize the coccygeal bone (coccygeal vertebrae) clearly due to the flatus. Therefore, in such a case, an original point may be set to a median point of a line segment to connect a left head of femur and a right head of femur. When the original point 112 has been designated (or determined), the CPU 2618 automatically draws a vertical line (i.e. the median line 110) from the original point 112. The median line 110 and the original point 112 may be overlaid on the smooth spine image and displayed in the display 263 (step S42). Once the original point 112 has been determined and the median line 110 has been drawn, the operator may then designate a terminal point 113 on the median line 110, which specifically determines a range of the median line in the calculation (step S43). For this designation, the operator may also use the mouse 262.

The CPU 2618 then calculates intersection points (X0, Y3) and (X0, Y2) where the median line 110 intersects with the smooth spine line 111 between the original point 112 (which is another intersection point (X0, Y1)) and the terminal point 113. Accordingly, a range between the intersection point (X0, Y1) (i.e. the original point 112) and the intersection point (X0, Y2) may be categorized as a zone 6. Another range between the intersection points (X0, Y2) and (X0, Y3) may be categorized as a zone 5. Further, a range between the intersection point (X0, Y3) and the terminal point 113 may be categorized as a zone 4 (step S44). In an example shown in FIG. 11 (B), 'Vertical-alignment' distances are calculated in the zones 5 and 6. When perpendicular line segments are dropped from the smooth spine line 111 to the median line 110, the 'Vertical-alignment' distance can be defined as a distance of a longest one of the perpendicular line segments. In FIG. 11(B), a perpendicular line segment 114 may be longest in the zone 6. In the zone 5, a perpendicular line segment 115 may be longest (step S45). These perpendicular line segments 114 and 115 may or may not be displayed in the display 263. Distances of the perpendicular line segments 114 and 116 are converted into actual distances (step S46). Results of the above calculations may be stored in the calculation result memory 2615 and also displayed in the display 263 in a manner of overlaying on the smooth spine image (step S47). Further, drawing information including one or more of the medial line 110, the original point 112, the terminal point 113, and the perpendicular line segments 114 and 115 may be stored as graphic data in the graphic data memory 2614. In addition to the above storage, in the hard disk 2616 stored may be the results of the calculation including a pixel, converted distances, distances of the perpendicular line segments 114 and 115, positions on the smooth spine line 111 where the perpendicular line segments 114 and 115 are dropped, the original point 112, and the terminal point 113 (step S48).

As an additional feature of the X-ray diagnosis apparatus 20, the data stored in the hard disk 2616 including the smooth spine image data and its attendant data such as the graphic data and the result of the calculation may be transferred by transmission to the workstation 31 and/or the laser imager 32 (step S49). Data to be transferred may alternatively be only the smooth spine image data. When the storage (and the transfer) has been completed, the calculation of the 'Vertical-alignment' distance may be terminated (step S50).

As described above, according to the first embodiment of the present invention, involvement of a human being system (the operator) may be reduced in the calculations of the Cobb angle and the 'Vertical-alignment' distance, compared to the prior art. This may result in improvement of the calculation accuracy and the reproducibility of the calculation result. Further, it may result in reduction of time required for obtaining the Cobb angle and the 'Vertical-alignment' distance.

Although the first embodiment of the present invention has exemplary advantages mentioned above, the first embodiment of the present invention still includes the manual operation using the mouse 262 by the operator in the process of determining the spine line during the calculation procedures. Such calculation still relies on experiences and skills of the operator, which leaves a possibility of deteriorating the calculation accuracy when an inexperienced or unskilled operator is involved in the calculation. In the following description, another embodiment of the present invention will be described as a second embodiment of the present invention, which may reduce the possibility of the deterioration in the first embodiment of the present invention.

(Second Embodiment)

Figure 12:
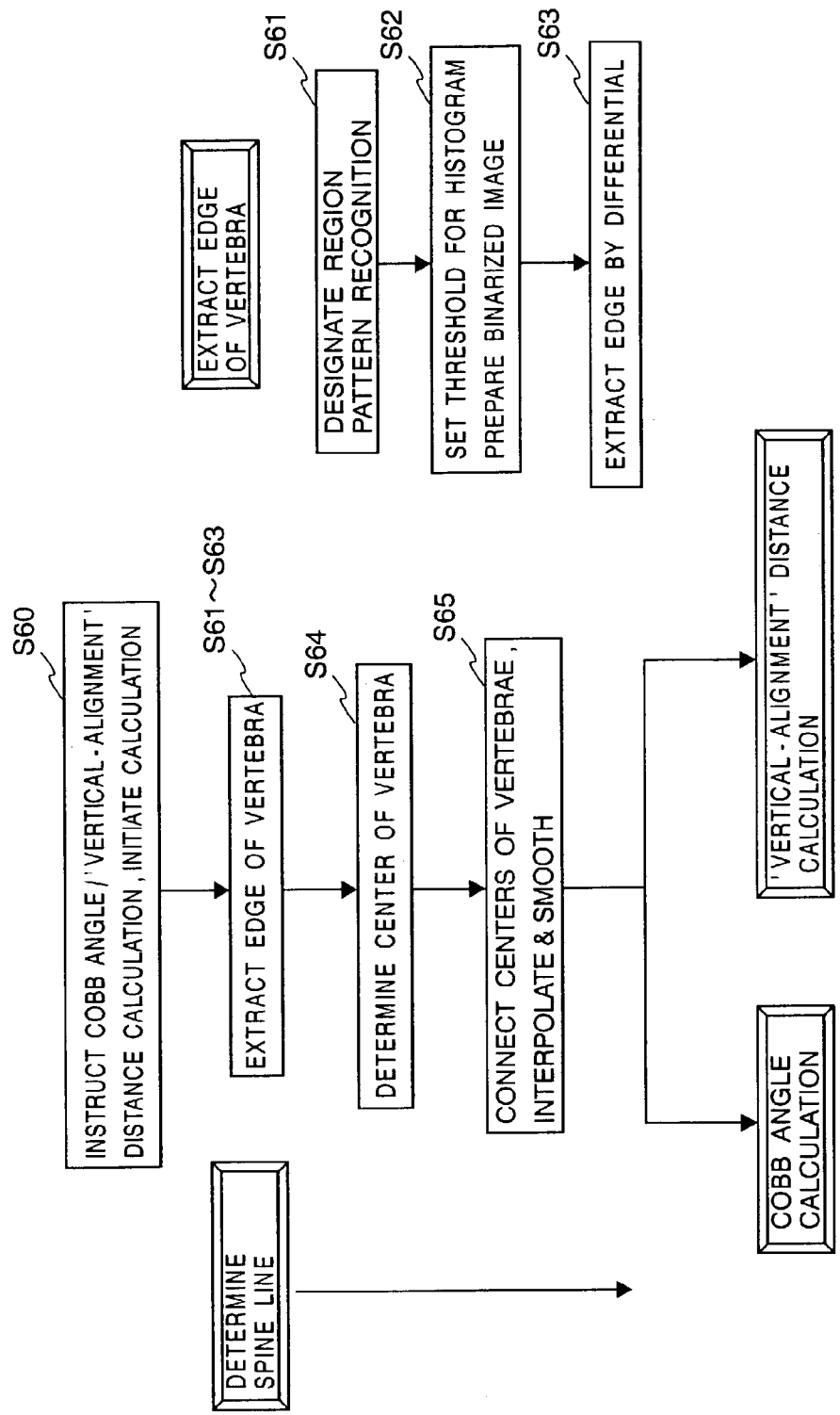
FIG. 12 is a flowchart showing an example of procedures of an automatic spine line drawing according to a second embodiment of the present invention.
Figure 13:
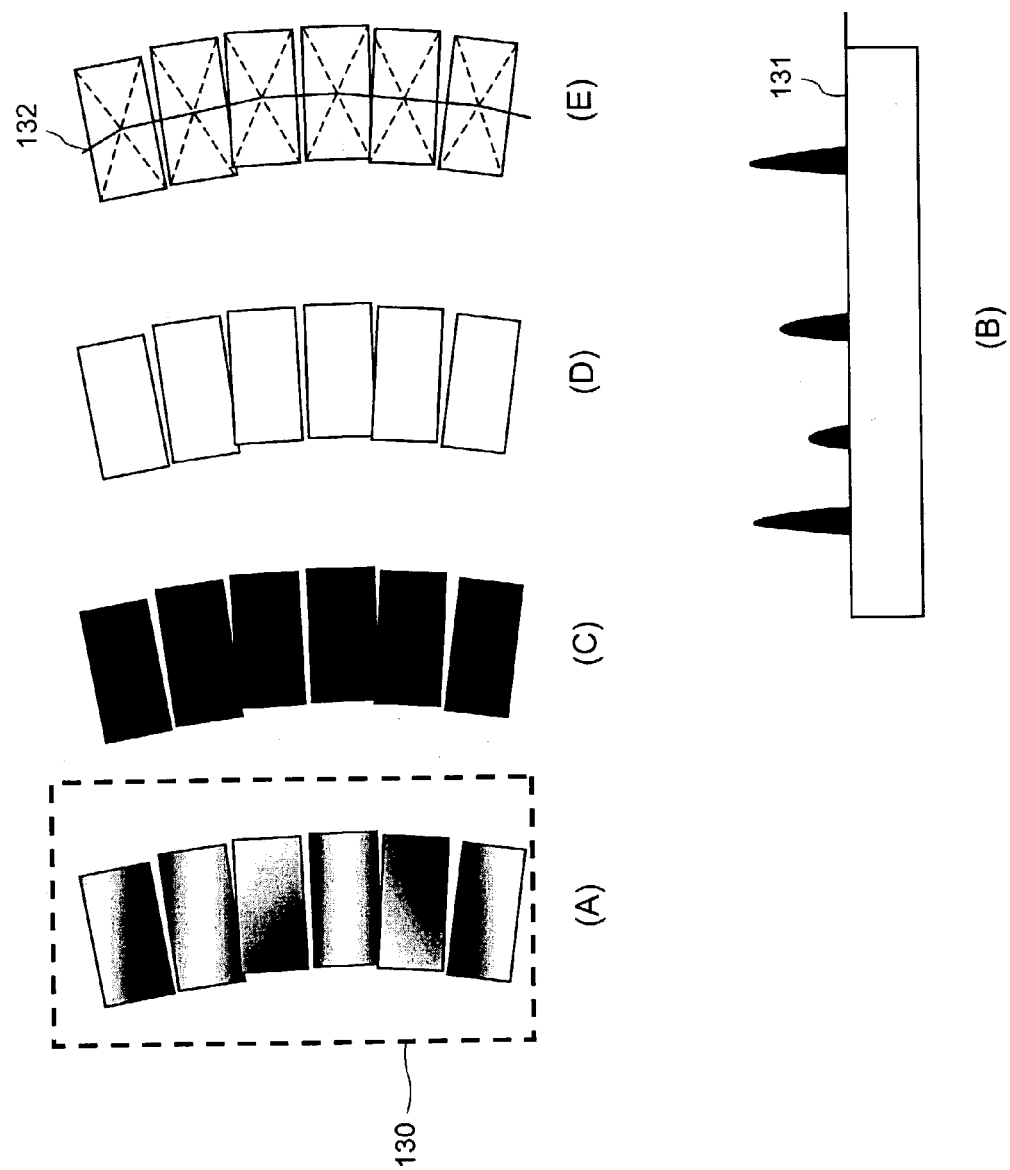
FIG. 13 is an illustration showing an example of processes of the automatic spine line drawing according to the second embodiment of the present invention.

The second embodiment of the present invention will be described with reference to FIGS. 12 and 13. FIG. 12 is a flowchart showing an example of procedures of an automatic spine line drawing according to the second embodiment of the present invention. FIG. 13 is an illustration showing an example of processes of the automatic spine line drawing according to the second embodiment of the present invention. In the second embodiment of the present invention, the synthesized spine image stored in the synthesized image memory 2613 is displayed in the display 263 through the display interface 2619. In the synthesized spine image, a representative point may be determined for each vertebra of the spine in the synthesized spine image. Every determined representative point may sequentially be connected by line segments. By smoothing the connected line segments, an automatically drawn spine line can be obtained. As one exemplary way of determining the representative points, each vertebra of the spine in the synthesized spine image displayed in the display 263 is recognized its outline as a square by a pattern recognition technique as shown in FIG. 13.

In general, there are introduced many kinds of the pattern recognition techniques. One of popular pattern recognition techniques may be as follows: a differential processing is made for an object image; in the object image, ridge lines are traced for edges with a greatest value; and accordingly, information of a shape of the object can be obtained. In another popular technique of the pattern recognition, an original image is binarized, and then its binarized edge is traced.

When the operator selects either the Cobb angle calculation command icon or the 'Vertical-alignment' distance calculation displayed in the display 263 by using the mouse 262, the selected calculation is instructed responsive to the operator's selection. The medical image processor 26 prepares to start procedures of the selected calculation (step S60).

In the preparation for the following actual calculation of either the Cobb angle or the 'Vertical-alignment' distance, first of all, each selected vertebra of the spine in the synthesized spine image is extracted by the pattern recognition in the following steps 61 to 63. For implementing the pattern recognition efficiently, a region 130 including two or more vertebrae of the spine may be designated as an object of the pattern recognition as shown in FIG. 13(A). The designation may be accomplished by circumscribing such vertebrae, using the mouse 262 (step S61). When the region for the pattern recognition has been designated, a histogram is prepared for the designated region of the synthesized spine image as shown in FIG. 13(B). According to the histogram, a predetermined threshold 131 is set and applied to signals of the brightness so as to exclude the signals below the threshold 131. Accordingly, a binarized image is prepared in the designated region 130 as shown in FIG. 13(C). The CPU 2618 then performs a two-dimensional differential processing on the binarized image and extracts edges of the binarized image (i.e., edges of the vertebrae). The extracted edges may be corrected for its fractures in accordance with or referring to baseline data of a vertebra shape in the CPU 2618 (step S63). Through the above steps S61 to S63, each of the vertebrae in the designated region 130 may be recognized as a square as shown in FIG. 13(D).

After the pattern recognition of the vertebrae in the designated region 130 as a collective of a plurality of squares, a center of each of the squares (vertebrae) is calculated in the CPU 2618. The center may be determined as an intersection point of diagonals (step S64). Centers of each adjacent two of the squares (vertebrae) are connected in a line segment. Alternatively, it may be possible to connect centers of each vicinal two of the squares (vertebrae) as long as the accuracy is allowed. In other words, for example, every one or two of centers of squares (vertebrae) may be connected in a line segment. Accordingly, centers of the squares (vertebrae in the designated region) are connected in a line 132 as shown in FIG. 13(E). The CPU 2618 interpolates and also smoothes the line 132. Accordingly, an automatic smooth spine line may be obtained (step S65). Smooth spine line data may be stored in the graphic data memory 2614. Information regarding the calculation of the automatic smooth spine line may be stored in the calculation result memory 2615.

In the step S64, the center of the square (vertebra) has been determined as the intersection point of the diagonals. The center, however may be a gravity point of the square.

Further, the designation of the region for the pattern recognition in step S61 may alternatively be accomplished by manually drawing a manual preliminary spine line by the operator, using the mouse 262. In this case, vertebrae on which the manual spine line has been drawn can be construed as objects for the pattern recognition.

Upon obtaining the automatic smooth spine line, either designated one of the Cobb angle calculation or the 'Vertical-alignment' distance calculation may be performed on the basis of the automatic smooth spine line. The Cobb angle calculation and the 'Vertical-alignment' distance calculation may be implemented in a manner similar to the description made for the first embodiment of the present invention.

According to the second embodiment of the present invention, a spine line is determined by the pattern recognition technique. In other words, the spine line is automatically calculated in the CPU 2618. Therefore, it may be possible to reduce a resulting difference between operators and a problem of the reproducibility in the follow-up observation of the spine. As a result, it may be possible to improve the accuracy of the calculation. In addition, it may also make it possible to further reduce time required for obtaining the Cobb angle and the 'Vertical-alignment' distance since the time of drawing the manual spine line by the operator is not required. The operator may be relieved from manually drawing the manual spine line required in the first embodiment of the present invention.

In the second embodiment of the present invention, the automatic smooth spine line has been obtained and used in the Cobb angle calculation and the 'Vertical-alignment' distance calculation. Regarding, however, the Cobb angle calculation, any type of the spine line may not be necessary for the calculation as long as each vertebra in the synthesized spine image is recognized in the pattern recognition.

(Third Embodiment)

Figure 14:
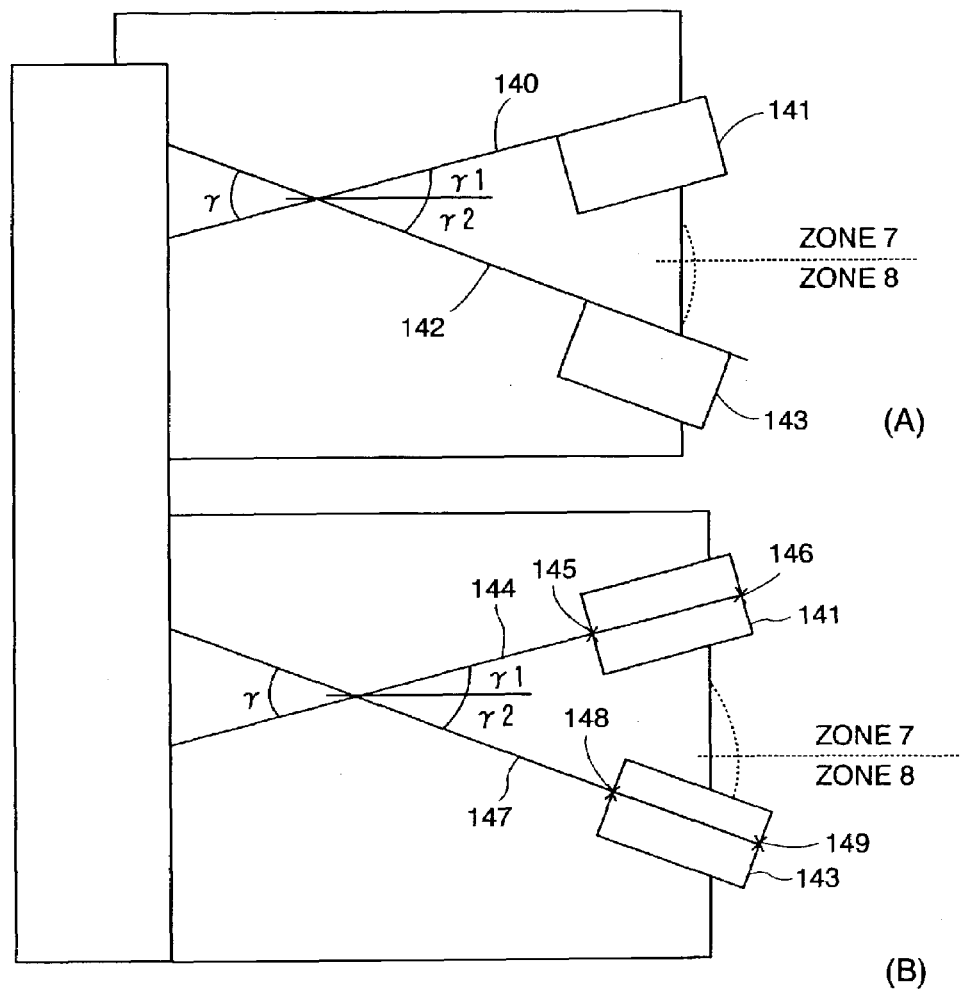
FIG. 14 is an illustration showing another example of the Cobb angle calculation according to a third embodiment of the present invention.

A third embodiment of the present invention will be described with reference to FIG. 14. FIG. 14 is an illustration showing another example of the Cobb angle calculation according to the third embodiment of the present invention. In the third embodiment of the present invention, the Cobb angle calculation described in the second embodiment of the present invention may be improved in its efficiency. The improved calculation is also based on condition that outlines of vertebrae in the designated region of the synthesized spine image are extracted as a collective of a plurality of squares in the pattern recognition in a manner similar to the second embodiment of the present invention.

For each of the extracted squares, the CPU 2618 draws a line segment (hereinafter referred to as an elongation) along an extension of an upper side of the each square. After the drawing, the CPU 2618 calculates gradients of the drawn elongations against a horizontal line (or angles between a horizontal line and the drawn elongations). In accordance with signs of the calculated gradients, the CPU 2618 divides the squares (vertebrae) into two or more zones. After the determination of the zones, the CPU 2618 selects one of elongations in each zone, which has a greatest gradient (angle) in the each zone. Further, the CPU 2618 calculates an angle between one elongation selected in a first zone and one elongation selected in a second zone adjacent to the first zone. The calculated angle can be construed as a Cobb angle. In this calculation, the CPU 2618 may simply add an angle between the horizontal line and the elongation selected in the first zone with an angle between the horizontal line and the elongation selected in the second zone.

For example, in FIG. 14(A), an elongation 140 is drawn along an upper side of a square (vertebra) 141 and selected as an elongation with a greatest gradient (angle γ 1) in a zone 7. Similarly, an elongation 142 is drawn along an upper side of a square (vertebra) 143 and selected as an elongation with a greatest gradient (angle γ 2) in a zone 8. The CPU 2618 adds the angle γ 1 with the angle γ 2 and obtains an angle γ as a Cobb angle.

The calculation result which may include the gradients, the angles, the elongations including the selected elongations, and the like, may be stored in the calculation result memory 2615. Further, the graphic data such as shown in FIG. 14(A) may also be stored with the above mentioned calculation result in the graphic data memory 2614. The graphic data with the calculation result stored in the graphic data memory 2614 are overlaid on the synthesized spine image data stored in the synthesized image memory 2613 in the display interface 2619. Accordingly, the synthesized spine image with the Cobb angle calculation result is displayed in the display 263. Still further, the calculated and/or obtained data stored or to be stored in the calculation result memory 2615 and/or the graphic data memory 2614 may also be stored as attendant data in the hard disk 2616.

FIG. 14(A) shows an example of drawing elongations along an upper side of a square (vertebra). Elongations, however, are not limited to such an example. Elongations may also be drawn along a lower side of a square (vertebra). In addition, when the upper side of the square is not parallel with the lower side of the square, a gradient (angle) averaged between the gradient (angle) of the upper side and the gradient (angle) of the lower side of the square may be used as a gradient (angle) of an elongation for the square. Still further, as shown in FIG. 14(B), an elongation 144 in the zone 7 may be determined as a line through a median point 145 of a left side of the square and a median point 146 of a right side of the square. Similarly, in the zone 8, an elongation 147 may be determined as a line through a median point 148 of a left side of the square and a median point 149 of a right side of the square.

Figure 15:
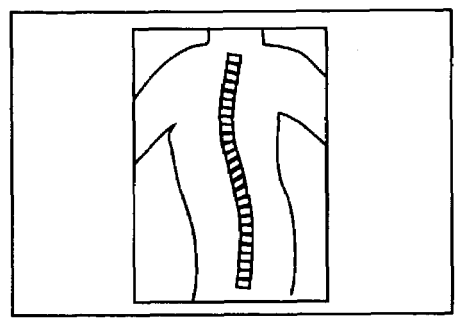
FIG. 15 is an illustration showing an example of image displays according to embodiments of the present invention.
Figure 15:
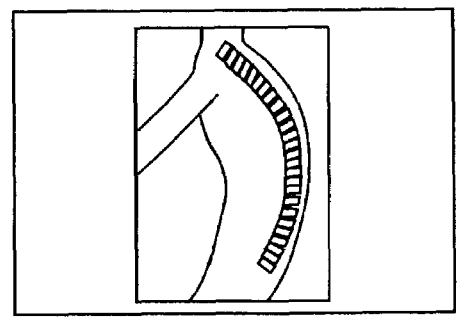
Figure 15:
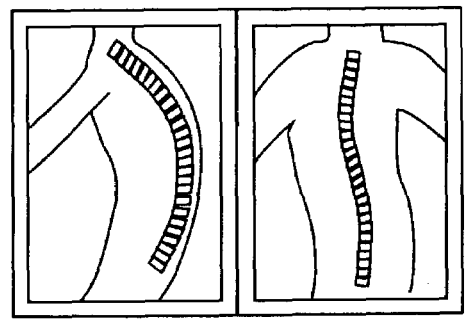
Figure 16:
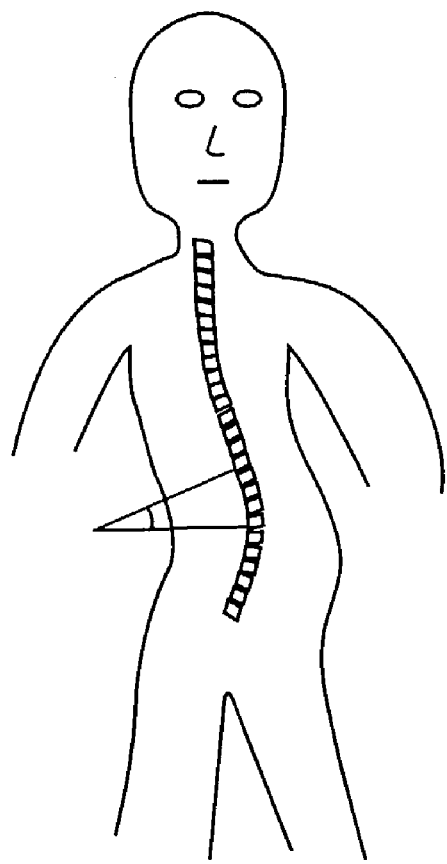
FIG. 16 is an illustration showing an example of synthesized spine images shown from different directions according to embodiments of the present invention.
Figure 16:
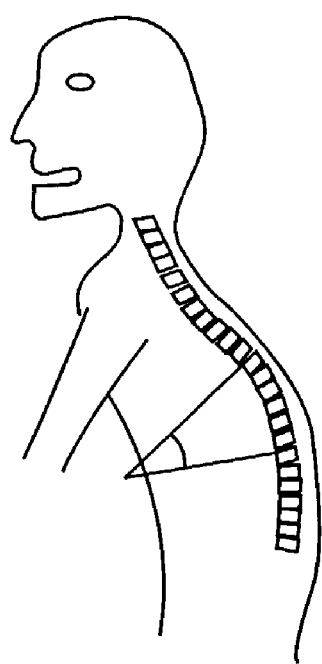

FIG. 15 is an illustration showing an example of image displays according to embodiments of the present invention. In embodiments of the present invention, a synthesized spine image displayed in the display 263 may not be limited to the synthesized spine image shown from a front (e.g. FIG. 16(A)) or from a back of the specimen P as shown in FIG. 15(A). When a synthesized spine image shown from a right side or from a left side (e.g. FIG. 16(B)) of the specimen P is obtained, such a synthesized spine image may be displayed in the display 263 as shown in FIG. 15(B). Further, if both of these synthesized spine images are obtained, both of the images may be displayed side by side as shown in FIG. 15(C). Alternatively, each of these images may be switched to be displayed independently.

According to the above description, the synthesized spine image has been based on the images obtained from the X-ray diagnosis apparatus. Embodiments of the present invention may not be limited to this, but may be applied to images obtained from other medical image equipments, such as, for example, an X-ray CT apparatus and an MRI apparatus. Further, the determination and/or the calculation of the automatic (smooth) spine line, the calculation of the Cobb angle, and the calculation of the 'Vertical-alignment' distance according to embodiments of the present invention may be handled independently as methods of determination or calculation, respectively.

Further, in the above-described embodiments of the present invention, the Cobb angle and the 'Vertical-alignment' distance have been described as the bow scale. The bow scale, however, may not be limited to those if there is an alternative bow scale to which embodiments of the present invention may be applicable.

In other embodiments of the present invention, it is contemplated that the bed 218 may move along the body axis of the specimen P, instead of or in addition to movement of the radiography system.

Additionally, when specific or nonspecific buttons are provided in the console 25, instructions may be made from such buttons, instead of or in addition to the selection of command icons displayed in the display 262.

Still further, in the embodiments of the present invention, the X-ray diagnosis apparatus or the medical image processing apparatus may have a random access memory (RAM), which can receive and store computer programs and applications as computer readable instructions in a temporary and/or non-volatile state. The X-ray diagnosis apparatus or the medical image processing apparatus may further have a hard disk drive as part of the controller for reading from and writing to a hard disk, a magnetic disk drive for reading from and writing to a magnetic disk, and/or an optical disk drive for reading from and writing to an optical disk (such as a CD, CDR, CD-RW, DVD, or other optical device). Those skilled in the art will appreciate that one or more of such memory, drives, and their respective media are examples of a computer program product for storing computer readable instructions, which when executed, may implement an embodiment of the present invention.

Accordingly, an apparatus, which does not incorporate features of embodiments of the present invention can benefit the features as long as the apparatus is equipped with a feature of reading and performing a computer readable program.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the above disclosure in the embodiments of the present invention is obtained.

What is claimed is:

1. A medical image processing apparatus which processes a medical image resulting from a medical image equipment, the apparatus comprising:
    an interface configured to obtain the medical image;
    a processor configured to determine a smooth line along an embowed part of a specimen in the medical image obtained by the interface; and
    a calculator configured to calculate a bow scale of the embowed part based on the smooth line determined by the processor,
    wherein the calculator is further configured to obtain tangent lines at predetermined points on the smooth line; obtain gradients, against a horizontal line, of perpendicular lines perpendicular to the tangent lines; and calculate a greatest angle, as the bow scale, between a first of the perpendicular lines with a positive gradient sign and a second of the perpendiculars line with a negative gradient sign based on the gradients.

2. The apparatus according to claim 1, wherein the embowed part represents a spine of the specimen.

3. The apparatus according to claim 2, wherein the smooth line is a line centered about the spine.

4. The apparatus according to claim 2, wherein the processor is further configured to extract a profile of each vertebra of the spine by a pattern recognition processing, obtain a center of the each vertebra based on the profile, and obtain the smooth line through the center of the each vertebra.

5. The apparatus according to claim 4, further comprising an input device coupled to the processor, the input device being configured to designate a range of the spine for the pattern recognition processing, and wherein the processor extracts the profile of each vertebra of the spine in the range designated by the input device.

6. The apparatus according to claim 2, wherein the processor comprises:
pattern recognition means for pattern recognizing each vertebra of the spine;
line segment means for drawing a plurality of line segments, wherein each of the line segments is between centers of two of the vertebrae recognized by the pattern recognition means; and
smoothing means for smoothing the line segments drawn by the line segment means so as to determine the smooth line.

7. The apparatus according to claim 6, wherein the two of the vertebrae are next to each other.

8. The apparatus according to claim 6, wherein the pattern recognition means is further configured to binarize the medical image obtained by the interface, differentiate the binarized medical image, and extract a profile of the vertebra.

9. The apparatus according to claim 1, wherein the embowed part represents a leg of the specimen.

10. The apparatus according to claim 1, wherein the medical image equipment is an X-ray diagnosis apparatus.

11. The apparatus according to claim 1, wherein the apparatus is incorporated in the medical image equipment.

12. The apparatus according to claim 1, wherein the bow scale represents a Cobb angle.

13. The apparatus according to claim 1, wherein the bow scale represents a Vertical-alignment distance.

14. The apparatus according to claim 1, further comprising a display configured to display the medical image with the smooth line and the bow scale.

15. The apparatus according to claim 1, further comprising:
a display configured to display the medical image; and
a drawing member configured to draw a manual line along the embowed part based on the medical image displayed in the display; and
wherein the processor further comprises smoothing means for smoothing the manual line drawn by the drawing member so as to determine the smooth line.

16. The apparatus according to claim 1, wherein the calculator is further configured to draw a median line for the smooth line, calculate distances between the median line and the smooth line at predetermined points on the smooth line, and output a longest distance of the calculated distances as the bow scale.

17. The apparatus according to claim 1, further comprising a display configured to display side by side a first image radiographed from a first direction of the specimen and a second image radiographed from a second-direction of the specimen.

18. The apparatus according to claim 1, further comprising a display configured to independently display one of a first image radiographed from a first direction of the specimen and a second image radiographed from a second direction of the specimen, the first image and the second image being portions of the medical image.

19. A medical image processing apparatus which processes a medical image resulting from a medical image equipment, the apparatus comprising:
an interface configured to obtain the medical image;
a processor configured to determine a smooth line along an embowed part of a specimen in the medical image obtained by the interface; and
a calculator configured to calculate a bow scale of the embowed part based on the smooth line determined by the processor,
wherein the calculator is further configured to:
obtain tangent lines at predetermined points on the smooth line;
obtain angles between a horizontal line and perpendicular lines perpendicular to the tangent lines;
find a first point of the predetermined points where an angle of the angles is substantially zero degrees;
find a second point of the predetermined points where a first absolute angle of the angles is greatest;
find a third point of the predetermined points where a second absolute angle of the angles is greatest, wherein the first point is between the second point and the third point along the smooth line;
add the first absolute angle and the second absolute angle to determine an added angle; and
output the added angle as the bow scale.

20. The apparatus according to claim 19, wherein the embowed part represents a spine of the specimen.

21. The apparatus according to claim 20, wherein the smooth line is a line centered about the spine.

22. The apparatus according to claim 20, wherein the processor is further configured to extract a profile of each vertebra of the spine by a pattern recognition processing, obtain a center of the each vertebra based on the profile, and obtain the smooth line through the center of the each vertebra.

23. The apparatus according to claim 22, further comprising an input device coupled to the processor, the input device being configured to designate a range of the spine for the pattern recognition processing, and wherein the processor extracts the profile of each vertebra of the spine in the range designated by the input device.

24. The apparatus according to claim 20, wherein the processor comprises:
pattern recognition means for pattern recognizing each vertebra of the spine;
line segment means for drawing a plurality of line segments, wherein each of the line segments is between centers of two of the vertebrae recognized by the pattern recognition means; and
smoothing means for smoothing the line segments drawn by the line segment means so as to determine the smooth line.

25. The apparatus according to claim 24, wherein the two of the vertebrae are next to each other.

26. The apparatus according to claim 24, wherein the pattern recognition means is further configured to binarize the medical image obtained by the interface, differentiate the binarized medical image, and extract a profile of the vertebra.

27. The apparatus according to claim 19, wherein the embowed part represents a leg of the specimen.

28. The apparatus according to claim 19, wherein the medical image equipment is an X-ray diagnosis apparatus.

29. The apparatus according to claim 19, wherein the apparatus is incorporated in the medical image equipment.

30. The apparatus according to claim 19, wherein the bow scale represents a Cobb angle.

31. The apparatus according to claim 19, wherein the bow scale represents a Vertical-alignment distance.

32. The apparatus according to claim 19, further comprising a display configured to display the medical image with the smooth line and the bow scale.

33. The apparatus according to claim 19, further comprising:
   a display configured to display the medical image; and
   a drawing member configured to draw a manual line along the embowed part based on the medical image displayed in the display; and
   wherein the processor further comprises smoothing means for smoothing the manual line drawn by the drawing member so as to determine the smooth line.

34. The apparatus according to claim 19, wherein the calculator is further configured to draw a median line for the smooth line, calculate distances between the median line and the smooth line at predetermined points on the smooth line, and output a longest distance of the calculated distances as the bow scale.

35. The apparatus according to claim 19, further comprising a display configured to display side by side a first image radiographed from a first direction of the specimen and a second image radiographed from a second-direction of the specimen.

36. The apparatus according to claim 19, further comprising a display configured to independently display one of a first image radiographed from a first direction of the specimen and a second image radio graphed from a second direction of the specimen, the first image and the second image being portions of the medical image.

37. A medical image processing apparatus which processes a medical image resulting from a medical image equipment, the apparatus comprising:
   an interface configured to obtain the medical image;
   a processor configured to determine a smooth line along an embowed part of a specimen in the medical image obtained by the interface; and
   a calculator configured to calculate a bow scale of the embowed part based on the smooth line determined by the processor,
   wherein the calculator is further configured to:
   draw a median line for the smooth line;
   calculate distances between the median line and the smooth line at predetermined points on the smooth line;
   find a first point of the smooth line where a first distance of the distances is zero;
   find a second point of the smooth line where a second distance of the distances is zero;
   find a third point of the smooth line between the first point and the second point where a third distance of the distances is longest; and
   output the third distance as the bow scale.

38. The apparatus according to claim 37, wherein the embowed part represents a spine of the specimen.

39. The apparatus according to claim 38, wherein the smooth line is a line centered about the spine.

40. The apparatus according to claim 38, wherein the processor is further configured to extract a profile of each vertebra of the spine by a pattern recognition processing, obtain a center of the each vertebra based on the profile, and obtain the smooth line through the center of the each vertebra.

41. The apparatus according to claim 40, further comprising an input device coupled to the processor, the input device being configured to designate a range of the spine for the pattern recognition processing, and wherein the processor extracts the profile of each vertebra of the spine in the range designated by the input device.

42. The apparatus according to claim 38, wherein the processor comprises:
   pattern recognition means for pattern recognizing each vertebra of the spine;
   line segment means for drawing a plurality of line segments, wherein each of the line segments is between centers of two of the vertebrae recognized by the pattern recognition means; and
   smoothing means for smoothing the line segments drawn by the line segment means so as to determine the smooth line.

43. The apparatus according to claim 42, wherein the two of the vertebrae are next to each other.

44. The apparatus according to claim 42, wherein the pattern recognition means is further configured to binarize the medical image obtained by the interface, differentiate the binarized medical image, and extract a profile of the vertebra.

45. The apparatus according to claim 37, wherein the embowed part represents a leg of the specimen.

46. The apparatus according to claim 37, wherein the medical image equipment is an X-ray diagnosis apparatus.

47. The apparatus according to claim 37, wherein the apparatus is incorporated in the medical image equipment.

48. The apparatus according to claim 37, wherein the bow scale represents a Cobb angle.

49. The apparatus according to claim 37, wherein the bow scale represents a Vertical-alignment distance.

50. The apparatus according to claim 37, further comprising a display configured to display the medical image with the smooth line and the bow scale.

51. The apparatus according to claim 37, further comprising:
   a display configured to display the medical image; and
   a drawing member configured to draw a manual line along the embowed part based on the medical image displayed in the display; and
   wherein the processor further comprises smoothing means for smoothing the manual line drawn by the drawing member so as to determine the smooth line.

52. The apparatus according to claim 37, wherein the calculator is further configured to draw a median line for the smooth line, calculate distances between the median line and the smooth line at predetermined points on the smooth line, and output a longest distance of the calculated distances as the bow scale.

53. The apparatus according to claim 37, further comprising a display configured to display side by side a first image radiographed from a first direction of the specimen and a second image radiographed from a second-direction of the specimen.

54. The apparatus according to claim 37, further comprising a display configured to independently display one of a first image radiographed from a first direction of the specimen and a second image radiographed from a second direction of the specimen, the first image and the second image being portions of the medical image.

55. A medical image processing apparatus which processes a medical image resulting from a medical image equipment, the apparatus comprising:
- an interface configured to obtain the medical image;
- a first processor configured to extract a profile of each vertebra of a spine in the medical image by a pattern recognition processing and obtain a gradient, against a horizontal line, of each of the vertebrae of the spine based on the extracted profile of each of the vertebrae; and
- a second processor configured to calculate a greatest angle, as a bow scale, between a first of the vertebrae of the spine with a positive gradient sign and a second of the vertebrae of the spine with a negative gradient sign based on the gradient of each of the vertebrae obtained by the first processor.

56. The apparatus according to claim 55, wherein, when the profile is generally in a shape of a four-sided polygon, the first processor obtains angles between a horizontal line and elongations each of which is in parallel with a same side of the profile of the each vertebra; and wherein the second processor finds a first of the elongations having a greatest of the angles in one direction and a second of the elongations having a greatest of the angles in an opposite direction, adds the angle of the first elongation and the angle of the second elongation; and outputs an added angle as the bow scale.

57. A method of measuring a predetermined part in a medical image resulting from a medical image equipment, the method comprising steps of:
- extracting a profile of each vertebra of a spine in the medical image by a pattern recognition processing;
- obtaining a gradient, against a horizontal line, of each of the vertebrae of the spine based on the extracted profile of each of the vertebrae; and
- calculating a greatest angle, as a bow scale, between a first of the vertebrae of the spine with a positive gradient sign and a second of the vertebrae of the spine with a negative gradient sign based on the gradient of each of the vertebrae obtained by the first processor.

58. A method of processing a medical image resulting from a medical image equipment, the method comprising:
- obtaining the medical image;
- determining a smooth line along an embowed part of a specimen in the medical image; and
- calculating a bow scale of the embowed part based on the smooth line,
- obtaining tangent lines at predetermined points on the smooth line;
- obtaining angles between a horizontal line and perpendicular lines perpendicular to the tangent lines;
- finding a first point of the predetermined points where an angle of the angles is substantially zero degrees;
- finding a second point of the predetermined points where a first absolute angle of the angles is greatest;
- finding a third point of the predetermined points where a second absolute angle of the angles is greatest, wherein the first point is between the second point and the third point along the smooth line;
- adding the first absolute angle and the second absolute angle to determine an added angle; and
- outputting the added angle as the bow scale.

59. A method of processing a medical image resulting from a medical image equipment, the method comprising:
- obtaining the medical image;
- determining a smooth line along an embowed part of a specimen in the medical image; and
- calculating a bow scale of the embowed part based on the smooth line,
- drawing a median line for the smooth line;
- calculating distances between the median line and the smooth line at predetermined points on the smooth line;
- finding a first point of the smooth line where a first distance of the distances is zero;
- finding a second point of the smooth line where a second distance of the distances is zero;
- finding a third point of the smooth line between the first point and the second point where a third distance of the distances is longest; and
- outputting the third distance as the bow scale.

* * * * *